(12) United States Patent
Turkson et al.

(10) Patent No.: US 8,895,746 B2
(45) Date of Patent: Nov. 25, 2014

(54) COMPOUNDS THAT SUPPRESS CANCER CELLS AND EXHIBIT ANTITUMOR ACTIVITY

(71) Applicants: University of Central Florida Research Foundation, Inc., Orlando, FL (US); The Governing Council of the University of Toronto, Toronto (CA)

(72) Inventors: James Turkson, Orlando, FL (US); Patrick Gunning, Mississauga (CA)

(73) Assignees: University of Central Florida Research Foundation, Inc., Orlando, FL (US); The Governing Council of the University of Toronto, Toronto (CA)

( * ) Notice: Subject to any disclaimer, the term of this patent is extended or adjusted under 35 U.S.C. 154(b) by 0 days.

(21) Appl. No.: 14/076,247

(22) Filed: Nov. 10, 2013

(65) Prior Publication Data

US 2014/0194468 A1 Jul. 10, 2014

Related U.S. Application Data

(63) Continuation of application No. 13/263,336, filed as application No. PCT/US2010/001021 on Apr. 5, 2010, now Pat. No. 8,586,749.

(60) Provisional application No. 61/166,865, filed on Apr. 6, 2009, provisional application No. 61/246,695, filed on Sep. 29, 2009.

(51) Int. Cl.
  C07D 211/60 (2006.01)
  C07C 315/00 (2006.01)
  A61K 31/196 (2006.01)
  A61K 31/451 (2006.01)

(52) U.S. Cl.
  CPC ............. *A61K 31/451* (2013.01); *A61K 31/196* (2013.01)
  USPC .......................................... 546/230; 562/430

(58) Field of Classification Search
  CPC ........................... A61K 31/196; A61K 31/451
  USPC .......................................... 546/230; 562/430
  See application file for complete search history.

(56) References Cited

U.S. PATENT DOCUMENTS 6,383,790 B1    5/2002  Shokat
2009/0069420 A1 *  3/2009  Turkson et al. ............... 514/518

OTHER PUBLICATIONS

Notice of Allowance mailed Jun. 10, 2014 for U.S. Appl. No. 13/813,916, filed May 10, 2013 (Inventors 13 James Turkson, et al.) (8 pages).
Response to Final Office Action filed May 13, 2014 for U.S. Appl. No. 13/813,916, filed May 10, 2013 (Inventors—James Turkson, et al.) (19 pages).
Final Office Action mailed May 5, 2014 for U.S. Appl. No. 13/813,916, filed May 10, 2013 (Inventors—James Turkson, et al.) (7 pages).

\* cited by examiner

*Primary Examiner* — John Mabry
(74) *Attorney, Agent, or Firm* — Ballard Spahr LLP

(57) ABSTRACT

The present invention provides compounds S3I-201.1066 (Formula 1) and S3I-201.2096 (Formula 2) as selective Stat3 binding agents that block Stat3 association with cognate receptor pTyr motifs, Stat3 phosphorylation and nuclear translocation, Stat3 transcriptional function, and consequently induced Stat3-specific antitumor cell effects in vitro and antitumor response in vivo.

20 Claims, 8 Drawing Sheets

COMPOUNDS THAT SUPPRESS CANCER CELLS AND EXHIBIT ANTITUMOR ACTIVITY

CROSS-REFERENCE TO RELATED APPLICATIONS

This application is a continuation of U.S. patent application Ser. No. 13/263,336, filed Feb. 6, 2012, now U.S. Pat. No. 8,586,749, which claims the priority of U.S. provisional application Ser. No. 61/166,865 filed on 6 Apr. 2009 and U.S. provisional patent application Ser. No. 61/246,695 filed on 29 Sep. 2009, each of which is incorporated herein by reference in its entirety.

STATEMENT REGARDING FEDERALLY SPONSORED RESEARCH OR DEVELOPMENT

This invention was made with government support under Grant Nos. R01 CA106439 and R01 CA128865 awarded by the National Institutes of Health. The government has certain rights in the invention.

The Sequence Listing submitted Mar. 24, 2014 as a text file named "26150_0004U4 Revised Sequence_Listing.txt," created on Mar. 24, 2014, and having a size of 2,616 bytes is hereby incorporated by reference pursuant to 37 C.F.R. §1.52(e)(5).

FIELD OF THE INVENTION

The present invention relates to the field of drug development and, more particularly, to compounds that inhibit cancer cells.

BACKGROUND OF THE INVENTION

Signal transduction proteins have increased importance in carcinogenesis and tumor formation and represent attractive targets for the development of novel anticancer therapeutics.

The Signal Transducer and Activator of Transcription (STAT) family of proteins are cytoplasmic transcription factors with important roles in mediating responses to cytokines and growth factors, including promoting cell growth and differentiation, and inflammation and immune responses (1,2). Normal STATs activation is initiated by the phosphorylation of a critical tyrosine residue upon the binding of cytokines or growth factors to their cognate receptors. The phosphorylation is induced by growth factor receptor tyrosine kinases, or cytoplasmic tyrosine kinases, including Janus kinases or the Src family kinases. While pre-existing dimers have been detected (3,4), phosphorylation is observed to induce dimerization between two STAT monomers through a phosphotyrosine interaction with the SH2 domain. In the nucleus, active STAT dimers bind to specific DNA-response elements in the promoters of target genes and regulate gene expression.

It is now well established that aberrant activation of the member of the family, Stat3 contributes to malignant transformation and tumorigenesis. Aberrant Stat3-mediated oncogenesis and tumor formation is due in part to the transcriptional upregulation of critical genes, which in turn lead to dysregulation of cell growth and survival, and the promotion of angiogenesis (2,5-11) and tumor immune-tolerance (12, 13). Thus, targeting of aberrant Stat3 signaling would provide a novel strategy for treating the wide variety of human tumors that harbor abnormal Stat3 activity.

The critical step of dimerization (14) between two monomers within the context of STAT activation presents an attractive strategy to interfere with Stat3 activation and functions and this approach has been exploited in prior work (15-25). Leading agents from those earlier studies have been explored for rational design in conjunction with molecular modeling of the binding to the Stat3 SH2 domain (18,19), per the X-ray crystal structure of the Stat3 homodimer (26). One of those leads, S3I-201 (18) had previously been shown to exert antitumor effects against human breast cancer xenografts via mechanisms that involve the inhibition of aberrant Stat3.

In the present study, key structural information from the computational modeling of S3I-201 bound to the Stat3 SH2 domain facilitated the design of novel analogs of which S3I-201.1066 and S3-201.2096 show improved Stat3-inhibitory activity. Both S3I-210.1066 and S3I-201.2096 inhibit Stat3 activity with $IC_{50}$ values of 35 and 45 µM, respectively. This disclosure presents evidence that S3I-201.1066 interacts with the Stat3 protein and disrupts Stat3 binding to its cognate pTyr peptide of receptors. Furthermore, S3I-201.1066 induces antitumor cell effects selectively in malignant cells harboring aberrant Stat3 and antitumor response in vivo in human breast xenografts.

SUMMARY OF THE INVENTION

With the foregoing in mind, the present invention advantageously provides a useful expansion of several prior studies that have provided the proof-of-concept for the therapeutic effects of Stat3 inhibitors in human tumors. The molecular modeling of the phosphotyrosine (pTyr)-SH2 domain interaction in Stat3:Stat3 dimerization, combined with in silico structural analysis of the previously reported Stat3 dimerization disruptor, S3I-201, has furnished a diverse set of analogs.

Herein we disclose that compounds S3I201.1066 and S3I-201.2096 selectively inhibit Stat3 DNA-binding activity in vitro, with $IC_{50}$ values of 35 and 45 µM, respectively. In vitro biochemical and biophysical studies show that S3I-201.1066 interacts with Stat3 or the SH2 domain, with an affinity (KD) of 2.74 µM, and disrupts Stat3 binding to the cognate pTyr-peptide motif, with an $IC_{50}$ value of 23 µM. Accordingly, S3I-201.1066 blocks Stat3 association with the epidermal growth factor (EGF) receptor in EGF-stimulated fibroblasts or in cancer cells, consequently inhibiting Stat3 phosphorylation, nuclear translocation and transcriptional activity, without affecting the $Erk^{MAPK}$ pathway.

Furthermore, treatment with S3I-201.1066 selectively suppressed the growth, viability, survival and malignant transformation of human breast (MDA-MB-231) and pancreatic (Panc-1) cancer lines and v-Src-transformed mouse fibroblasts harboring aberrant Stat3, and down-regulated the expression of known Stat3-regulated genes, including c-Myc, Bcl.xL, the matrix metalloproteinase 9, and VEGF. Importantly, treatment with S3I-201.1066 induced strong tumor regression in xenografts of the human breast cancer line MDA-MB-231.

Taken together, the present disclosure identifies compounds S3I-201.1066 (Formula 1) and S3I-201.2096 (Formula 2) as selective Stat3 binding agents that block Stat3 association with cognate receptor pTyr motifs, Stat3 phosphorylation and nuclear translocation, Stat3 transcriptional function, and consequently induced Stat3-specific antitumor cell effects in vitro and antitumor response in vivo.

Accordingly, the present disclosure provides a novel compound, analog of S3I-201, according to Formula 1, as set forth below and in FIG. 1, and salts thereof.

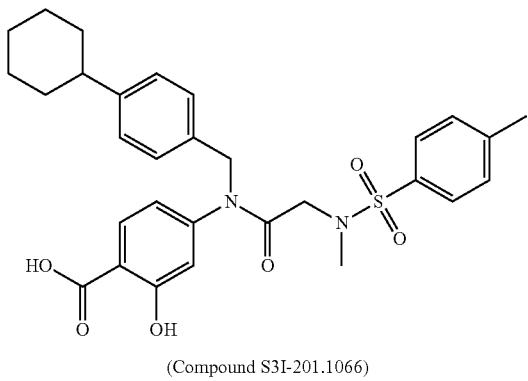

(Compound S3I-201.1066)

Formula 1

The disclosure also contemplates that the invention includes the compound of Formula 1 used in a pharmaceutical composition acceptable for administration to a patient.

Those skilled in the art should recognize that the compounds of this invention may be administered to mammals, preferably humans, either alone or in combination with pharmaceutically acceptable carriers, excipients or diluents, in a pharmaceutical composition, according to standard pharmaceutical practice. The compounds can be administered by any route but are preferably administered parenterally, including by intravenous, intramuscular, intraperitoneal, subcutaneous, rectal and also by topical routes of administration.

The term "composition" is intended to encompass a product comprising the disclosed compounds in amounts effective for causing the desired effect in the patient, as well as any product which results, directly or indirectly, from combination of the specific ingredients. However, the skilled should understand that when a composition according to this invention is administered to a human subject, the daily dosage of active agents will normally be determined by the prescribing physician with the dosage generally varying according to the age, weight, sex and response of the individual patient, as well as the severity of the patient's symptoms.

The terms pharmaceutical composition, pharmaceutically and/or pharmacologically acceptable for administration to a patient refer to molecular entities and/or compositions that do not produce an adverse, allergic and/or other untoward reaction when administered to a subject, be it animal or human, as appropriate.

As known to the skilled, a pharmaceutically acceptable composition or carrier includes any and/or all solvents, dispersion media, coatings, antibacterial and/or antifungal agents, isotonic and/or absorption delaying agents and/or the like. The use of such media and/or agents for pharmaceutical active substances is well known in the art. Except insofar as any conventional media and/or agent is incompatible with the active ingredient, its use in the therapeutic compositions is contemplated. Supplementary active ingredients can also be incorporated into the compositions. For administration, preparations should meet sterility, pyrogenicity, general safety and/or purity standards as required by FDA Office of Biologics standards.

The skilled will find additional guidance in preparation of pharmaceutically acceptable compositions by consulting United States Pharmacopeia (USP) or other similar treatises employed in the pharmaceutical industry.

The novel compound of Formula 1, given above, may be used in various methods of treatment, for example: a method of treatment effective to inhibit a cancer cell by contacting the cell with said compound; a method of treatment effective to inhibit a human pancreatic cancer cell by contacting the cell with said compound; a method of treatment effective to inhibit a human breast cancer cell by contacting the cell with said compound; a method of treatment effective to inhibit a cell characterized by an aberrant level of Stat3 by contacting the cell with said compound; to inhibit a cell characterized by an aberrant level of Stat3 by contacting the cell with said compound so as to selectively bind Stat3; to down-regulate expression of Stat3-regulated genes in a cell by contacting the cell with said compound; to selectively inhibit Stat3-DNA binding activity in a cell by contacting the cell with said compound, to block Stat3 association with epidermal growth factor receptor in EGF-stimulated fibroblasts by contacting the fibroblasts with said compound; and to inhibit tumor cells dependent on aberrant Stat3-mediated oncogenesis by contacting the tumor cells with said compound so as to interfere with Stat3 function.

The present disclosure also contemplates a second compound, related to the compound of Formula 1 by both being analogs of S3I-201. This second compound is shown below according to Formula 2 and salts thereof.

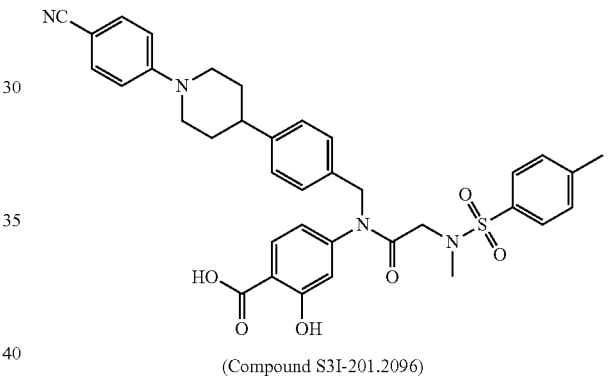

Formula 2

(Compound S3I-201.2096)

The compound of Formula 2 has properties that parallel those of the compound of Formula 1 and may be employed in a likewise manner, as described above.

As used herein, the terms "treat," "treating" or "method of treatment" refer to both therapeutic treatment and prophylactic or preventive measures, wherein the object is to prevent or slow down (lessen) an undesired physiological change or disorder, such as the development or spread of cancer or other proliferation disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. For example, treatment with a compound of the invention may include reduction of undesirable cell proliferation, and/or induction of apoptosis and cytotoxicity.

"Treatment" can also mean prolonging survival as compared to expected survival if not receiving treatment. Those in need of treatment include those already with the condition or disorder as well as those prone to have the condition or disorder or those in which the condition or disorder is to be prevented or onset delayed. Optionally, the patient may be identified (e.g., diagnosed) as one suffering from the disease or condition (e.g., proliferation disorder) prior to administration of the Stat3 inhibitor of the invention.

The terms "effective to inhibit" or "growth inhibitory amount" of the compounds of the invention refer to an amount which reduces (i.e., slows to some extent and preferably stops) proliferation of a target cell, such as a tumor cell, either in vitro or in vivo, irrespective of the mechanism by which cell growth is inhibited (e.g., by cytostatic properties, cytotoxic properties, etc.).

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which.

DETAILED DESCRIPTION OF PREFERRED EMBODIMENTS

Figure 1:
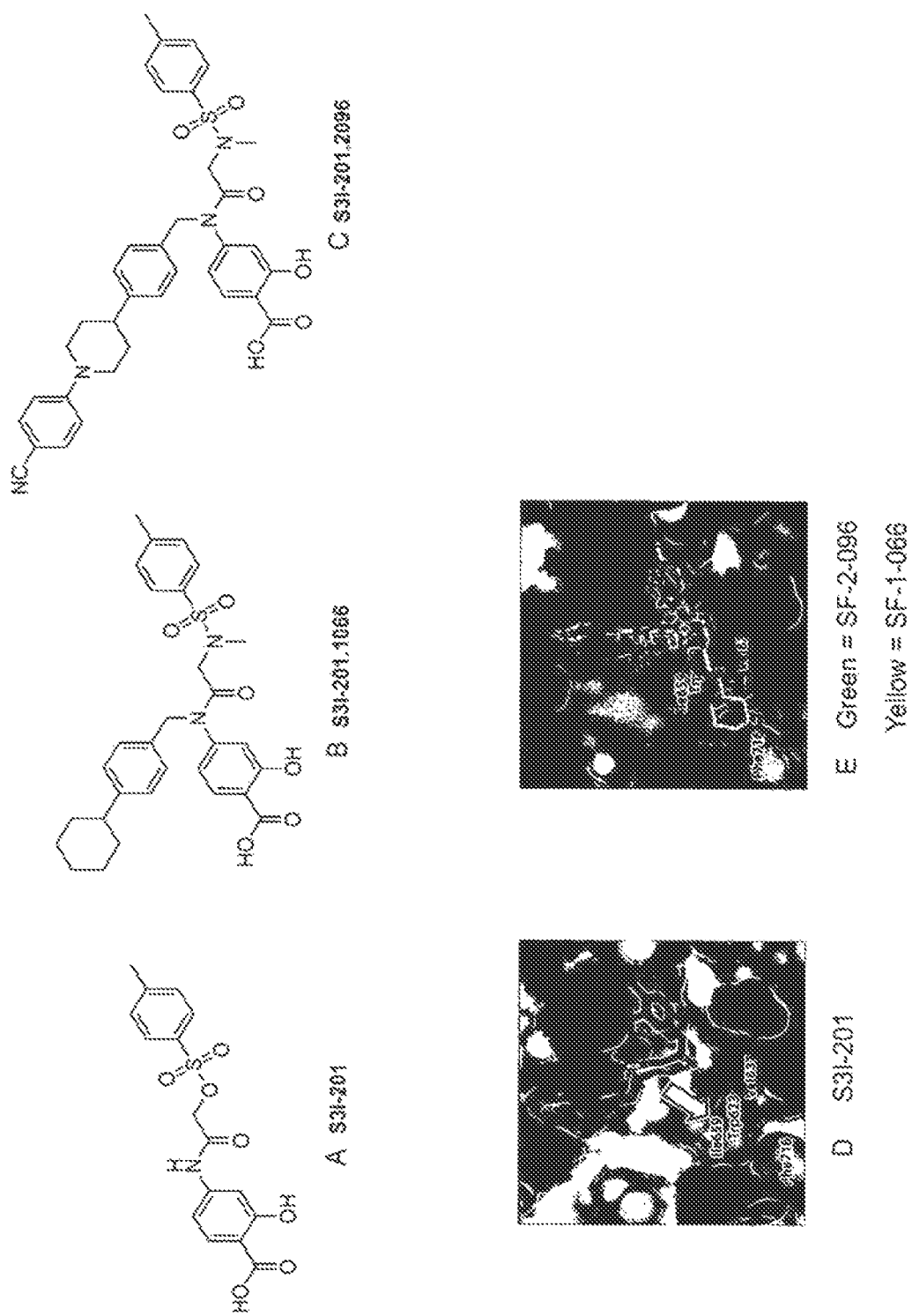
FIG. 1(A-C), illustrates structures of (A) S3I-201, (B) S3I-201.1066 and (C) S3I-201.2096; D and E, GOLD docking of (D) S3I-201 (green), and (E) S3I-201.1066 (yellow) and S3I-201.2096 (green) to the SH2 domain of Stat3; arrow denotes potential binding sub-pocket.

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, or other references mentioned or cited herein are incorporated by reference in their entirety. In case of conflict, the present specification, including any definitions, will control. In addition, those of skill in the art should recognize that the materials, methods and examples given are illustrative in nature only and not intended to be limiting. Accordingly, this invention may be embodied in many different forms and should not be construed as limited to the illustrated embodiments set forth herein. Rather, the illustrated embodiments are provided so that this disclosure will be thorough and complete, and will fully convey the scope of the invention to those skilled in the art. Other features and advantages of the invention will be apparent from the following detailed description, and from the claims.

The abbreviations used herein are: STAT, signal transducer and activator of transcription; PBST, phosphate-buffered saline Tween-200; HPDEC, normal human pancreatic duct epithelial cell line; Stat3−/−, Stat3 knockout mouse embryonic fibroblasts; PBS, phosphate-buffered saline; EMSA, electrophoretic mobility shift assay; Erk, extracellular signal-regulated kinase; FBS, fetal bovine serum; MMP-9, matrix metalloproteinases 9.

EXPERIMENTAL PROCEDURES

Cells and Reagents

Normal mouse fibroblasts (NIH3T3) and counterparts transformed by v-Src (NIH3T3/v-Src), v-Ras (NIH3T3/v-Ras) or overexpressing the human epidermal growth factor (EGF) receptor (NIH3T3/hEGFR), and the human breast cancer (MDA-MB-231) and pancreatic cancer (Panc-1) cells have all been previously reported (15,27-29). The normal human pancreatic duct epithelial cells (HPDEC) was a kind gift from Dr. Tsao, (OCI, UHN-PMH, Toronto) (30), Stat3 knockout mouse embryonic fibroblasts was generously provided by Dr. Poli (31), and the mouse thymic epithelial stromal cells (TE-71) was a generous gift from Dr. Farr (32). The Stat3dependent reporter, pLucTKS3 and the v-Src transformed mouse fibroblasts that stably express pLucTKS3 have been previously reported (15, 33). Cells were grown in Dulbecco's modified Eagle's medium (DMEM) containing 10% heat-inactivated fetal bovine serum, or in the case of HPDEC, they were grown in Keratinocyte-SFM media supplemented with 0.2 ng EGF, 30 μg/ml bovine pituitary extract and containing antimycol. Antibodies against Stat3, pY705Stat3, Src, pY416Src, Jak1, pJak1, Shc, pShc, Erk1/2, and pErk1/2 are from Cell Signaling Technology (Danvers, Mass.).

Cloning and Protein Expression

Coding regions for the murine Stat3 protein and Stat3 SH2 domain were amplified by PCR and cloned into vectors pET-44 Ek/LIC (Novagen) and pET SUMO (Invitrogen), respectively.

The primers used for amplification were: Stat3 Forward: GACGACGACAAGATGGCTCAGTGGAACCAGCTGC (SEQ ID NO:1); Stat3 Reverse: GAGGAGAAGCCCGGT-TATCACATGGGGGAGGTAGCACACT (SEQ ID NO:2); Stat3-SH2 Forward: ATGGGTTTCATCAGCAAGGA (SEQ ID NO:3); Stat3-SH2 Reverse: TCACCTACAGTACTTTC-CAAATGC (SEQ ID NO:4).

Clones were sequenced to verify the correct sequences and orientation. His-tagged recombinant proteins were expressed in BL21(DE3) cells, and purified on Ni-ion sepharose column.

Nuclear Extract Preparation, Gel Shift Assays, and Densitometric Analysis

Nuclear extract preparations and electrophoretic mobility shift assay (EMSA) were carried out as previously described (28,33). The $^{32}$P-labeled oligonucleotide probes used were hSIE (high affinity sis-inducible element from the c-fos gene, m67 variant, 5'AGCTTCATTTCCCGTAAATCCCTA; SEQ ID NO:5) that binds Stat1 and Stat3 (34) and MGFe (mammary gland factor element from the bovine β-casein gene promoter, 5'-AGATTTCTAGGAATTCAA; SEQ ID NO:6) for Stat1 and Stat5 binding (35,36). Except where indicated, nuclear extracts were pre-incubated with compound for 30 min at room temperature prior to incubation with the radio-labeled probe for 30 min at 30° C. before subjecting to EMSA analysis. Bands corresponding to DNA-binding activities were scanned and quantified for each concentration of compound using ImageQuant and plotted as percent of control (vehicle) against concentration of compound, from which the $IC_{50}$ values were derived, as previously reported (37).

Immunoprecipitation and SDS-PAGE/Western Blotting Analysis

Immunoprecipitation from whole-cell lysates and SDS/PAGE and Western blotting analysis were performed as previously described (33,38). Primary antibodies used were anti-Stat3, pY705Stat3, pY416Src, Src, pErk1/2, Erk1/2, pJak1, Jak1, pShc, Shc, Grb 2, c-Myc, Bcl-xL, MMP-9, and β-Actin (Cell Signaling, Danvers), and VEGF (Santa Cruz Biotech, Santa Cruz).

Cell Viability and Proliferation Assay

Cells in culture in 6-well or 96-well plates were treated with or without S3I-201.1066 for 24-144 h and subjected to CyQuant cell proliferation assay (Invitrogen Corp/Life Technologies Corp, Carlsbad, Calif.), or harvested, and the viable cells counted by trypan blue exclusion with phase contrast microscopy.

Immunofluorescence Imaging/Confocal Microscopy

NIH3T3/hEGFR cells were grown in multi-cell plates, serum-starved for 8 h and treated with or without S3I-201.1066 for 30 min prior to stimulation by rhEGF (1 g/ml) for 10 min. Cells were fixed with ice-cold methanol for 15 min, washed 3 times in PBS, permeabilized with 0.2% Triton® X-100 for 10 min, and further washed 3-4 times with PBS. Specimens were then blocked in 1% BSA for 30 min and incubated with EGFR (Santa Cruz) or Stat3 (Cell Signaling Tech) antibody at 1:50 dilution at 4° C. overnight. Subsequently, cells were rinsed 4-5 times in PBS, incubated with Alexafluor 546 rat antibody for EGFR detection and Alexa fluor 488 rabbit antibody for Stat3 detection (Invitrogen) for 1 h at room temperature in the dark. Specimens were then washed 5 times with PBS, covered with cover slides with VECTASHIELD mounting medium containing DAPI, and examined immediately under a Leica TCS SP5 confocal microscope (Germany) at appropriate wavelengths. Images were captured and processed using the Leica TCS SP 5 software.

Soft-Agar Colony Formation Assay

Colony formation assays were carried out in 6-well dishes, as described previously (16,37). Briefly, each well contained 1.5 ml of 1% agarose in Dulbeco's modified Eagle's medium as the bottom layer and 1.5 ml of 0.5% agarose in Dulbeco's modified Eagle's medium containing 4000 or 6000 NIH3T3/v-Src or NIH3T3/v-Ras fibroblasts, respectively, as the top layer. Treatment with S3I201.1066 was initiated 1 day after seeding cells by adding 80 μl of medium with or without S3I20.1.1066, and repeating every 3 days, until large colonies were evident. Colonies were quantified by staining with 20 μl of 1 mg/ml crystal violet, incubating at 37° C. overnight, and counting the next day under phase contrast microscope.

Fluorescence Polarization Assay

Fluorescence Polarization (FP) Assay was conducted as previously reported (23), with some modification using the phospho-peptide, 5-carboxyfluorescein-GpYLPQTV-NH2 (phosphorylated SEQ ID NO:7) (where pY represents phospho-Tyr) as probe and Stat3. The FP assay was used to evaluate the binding of agents to Stat3 and to determine the ability to disrupt the Stat3:pTyr peptide interaction. A fixed concentration of the fluorescently-labeled peptide probe (10 nM) was incubated with increasing concentration of the Stat3 protein for 30 min at room temperature in the buffer, 50 mM NaCI, 10 mM HEPES, 1 mM EDTA, 0.1% Nonidet P-40, and the fluorescent polarization measurements were determined using the POLARstar Omega (BMG LABTECH, Durham, N.C.), with the set gain adjustment at 35 mP. The Z' value was derived per the equation $Z'=1-(3\ SD_{bound}+3\ SD\ f_{ree})/(mP_{bound}-mP_{free})$, where SD is the standard deviation and mP is the average of fluorescence polarization. In the bound state, 10 nM 5-carboxyfluorescein-GpYLPQTV-NH2 (phosphorylated SEQ ID NO:7) was incubated with 150 nM purified Stat3 protein, while the free (unbound) state was the same mixture, but incubated with an additional 10 IJM unlabeled Ac-GpYLPQTV-NH2 (phosphorylated SEQ ID NO:7). For evaluating agents, Stat3 protein (150 nM) was incubated with serial concentrations of S3I-201.1066 at 30° C. for 60 min in the indicated assay buffer conditions. Prior to the addition of the fluorescence probe, the protein:S3I-201.1066 mixtures were allowed to equilibrate at room temperature for 15 min. Probe was added at a final concentration of 10 nM and incubated for 30 min at room temperature following which the FP measurements were taken using the POLARstar Omega, with the set gain adjustment at 35 mP.

Surface Plasmon Resonance Analysis

SensiQ and its analysis software Qdat (ICX Technologies, Oklahoma City, Okla.) were used to analyze the interaction between agents and the Stat3 protein and to determine the binding affinity. Purified Stat3 was immobilized on a HisCap Sensor Chip by injecting 50 g/ml of Stat3 onto the chip. Various concentrations of S3I-201.1066 in running buffer (1×PBS, 0.5% DMSO) were passed over the sensor chip to produce response signals. The association and dissociation rate constants were calculated using the Qdat software. The ratio of the association and dissociation rate constants was determined as the affinity ($K_D$).

Colony Survival Assay

This was performed as previously reported (39). Briefly, cells were seeded as single-cell in 6-cm dishes (500 cells per well), treated once the next day with S3I-201.1066 for 48 h, and allowed to grow until large colonies were visible. Colonies were stained with crystal violet for 4 h and counted under phase-contrast microscope.

Wound Healing Assay for Migration

Wounds were made using pipette tips in monolayer cultures of cells in six-well plates. Cells were treated with or without increasing concentrations of S3I-201,1066 and allowed to migrate into the denuded area for 12-24 hours. The migration of cells was visualized at a 10× magnification using an Axiovert 200 Inverted Fluorescence Microscope (Zeiss, Göttingen Germany), with pictures taken using a mounted Canon Powershot A640 digital camera (Canon USA, Lake Success, N.Y.). Cells that migrated into the denuded area were quantified. Mice and in vivo tumor studies-Six-week-old female athymic nude mice were purchased from Harlan and maintained in the institutional animal facilities approved by the American Association for Accreditation of Laboratory Animal Care. Athymic nude mice were injected subcutaneously in the left flank area with $5 \times 10^6$ human breast cancer MDA-MB-231 cells in 100 μL of PBS. After 5 to 10 days, tumors of a diameter of 3 mm were established. Animals were grouped so that the mean tumor sizes in all groups were nearly identical, then given S3I-201.1066 intravenously at 3 mg/kg every 2 or every 3 days for 17 days and monitored every 2 or 3 days, and tumor sizes were measured with calipers. Tumor volume was calculated according to the formula $V=0.52 \times a^2 \times b$, where a, smallest superficial diameter, b, largest superficial diameter.

Statistical Analysis

Statistical analysis was performed on mean values using Prism GraphPad Software, Inc. (La Jolla, Calif.). The significance of differences between groups was determined by the paired t-test at $p<0.05^*$, $<0.01^{}$, and $<0.001^{*}$.

Results

Computer-Aided Design of S3I-201 Analogs as Stat3 Inhibitors.

Close structural analysis of the lowest Genetic Optimization for Ligand Docking (GOLD) (40) conformation of the lead Stat3 inhibitor, S3I-201 (yellow) ($IC_{50}$=86 μM for inhibition of Stat3:Stat3 (18)) (FIG. 1A) bound within the Stat3 SH2 domain (FIG. 1D), per the X-ray crystal structure of DNA-bound Stat3β homodimer (26) showed significant complementary interactions between the protein surface and the compound and identified key structural requirements for tight binding. Docking studies permitted in silico structural design of analogs of differing Stat3 SH2 domain-binding characteristics in order to derive Stat3 inhibitors of improved potency and selectivity. GOLD docking studies showed limited structural occupation of the Stat3-SH2 domain, identifying a potential means for improving inhibitor potency. The SH2 domain is broadly composed of three sub-pockets, only two of which are accessed by S3I-201 (FIG. 1D). Lead agent, S3I-201 (FIG. 1A) has a glycolic acid scaffold with its carboxylic acid condensed with a hetero-trisubstituted aromatic species to furnish the amide bond, and a hydroxyl moiety that has been tosylated. The ortho-hydroxybenzoic acid component is a known pTyr mimetic, and low energy GOLD docking studies consistently placed this unit in the pTyr-binding site, making hydrogen bonds and electrostatic interactions with Lys591, Ser611, Ser613 and Arg609. Due to the strength of such interactions between oppositely charged ions, it is likely that a considerable portion of the binding between the SH2 domain and S3I-201 arises from the pTyr mimetic. The Otosyl group binds in the mostly-hydrophobic pocket that is derived from the tetramethylene portion of the side chain of Lys592 and the trimethylene portion of the side chain of Arg595, along with Ile597 and Ile634. Given the potency of S3I-201 towards Stat3 inhibition, a rational synthetic program was undertaken to modify and optimize the core scaffold to furnish more potent analogs. We additionally exploited key hydrophobic interactions with Phe716, Ile659, Val637 and Trp623 (FIG. 1D) in generating compounds made of N-substituted (paracyclohexyl)benzyl analogs (FIGS. 1B and C).

A paper by Fletcher et al. entitled. Disruption of Transcriptionally Active Stat3 Dimers with Non-Phosphorylated, Salicylic Acid-Based Small Molecules: Potent in vitro and Tumor Cell Activities, which reports on the details of the design and synthesis of the series of S3I-201 analogs may be used by the skilled for guidance in synthesizing the novel compounds disclosed herein (41).

Inhibition of Stat3 DNA-Binding Activity.

Figure 2:
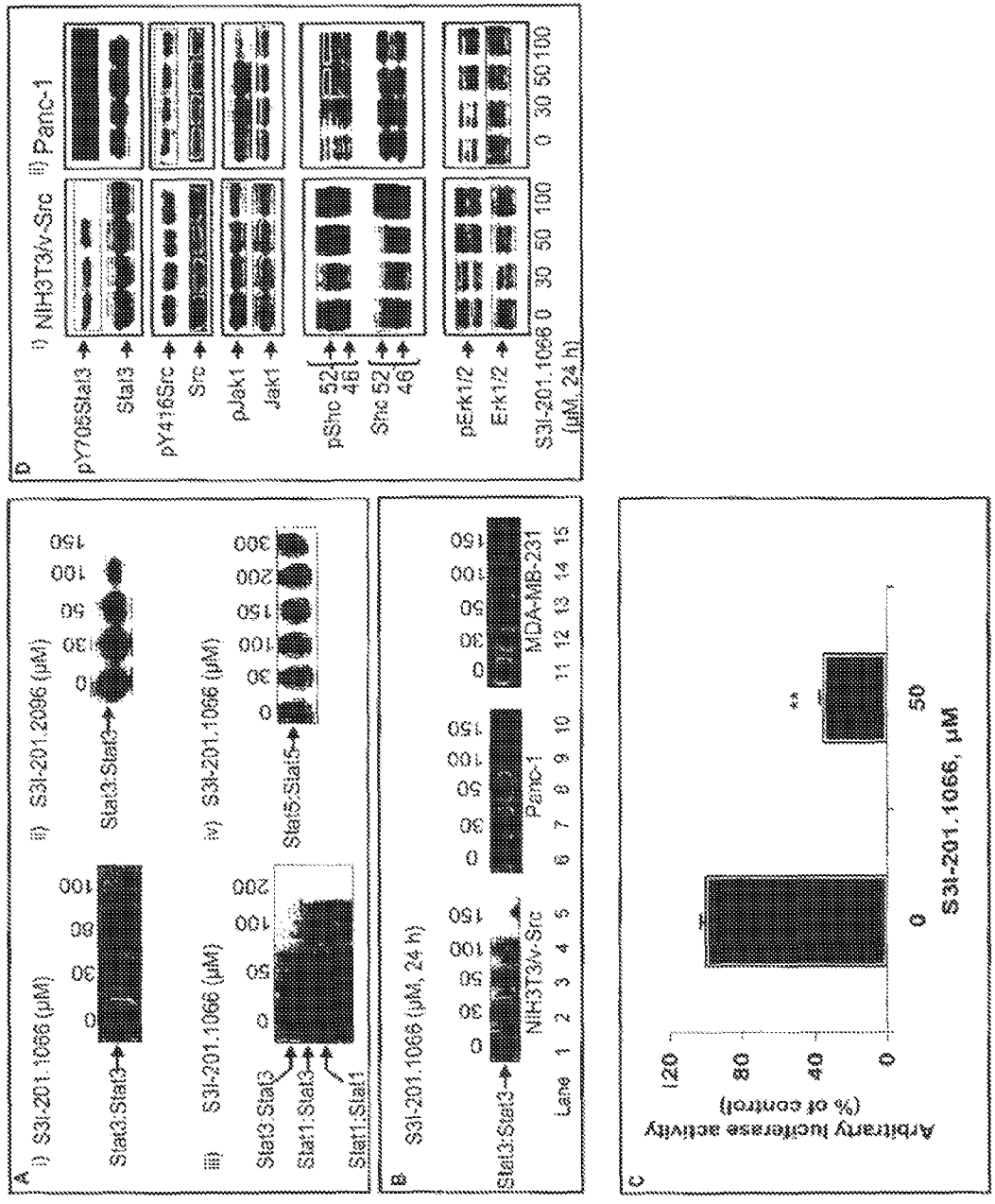
FIG. 2 shows effects of S3I-201.1066 and S3I-201.2096 on the activities of STATs, Src, Jak1, Shc, and Erks. (A) Nuclear extracts of equal total protein containing activated Stat1, Stat3, and/or Stat5 were pre-incubated with or without (i), (iii) and (iv) S3I-201.1066 or (ii) S3I-201.2096 for 30 min at room temperature prior to the incubation with the radiolabeled hSIE probe that binds Stat1 and Stat3 or the MGFe probe that binds Stat5 and subjecting to EMSA analysis; (B) Nuclear extracts of equal total protein prepared from malignant cells following 24-h treatment with or without S3I-201.1066 were subjected to in vitro DNA-binding assay using the radiolabeled hSIE probe and analyzed by EMSA; (C) Cytosolic extracts of equal total protein were prepared from 36-h S3I-201.1066-treated or untreated NIH3T3/v-Src fibroblasts that stably express the Stat3-dependent luciferase reporter (pLucTKS3) and analyzed for luciferase activity using a luminometer, and (D) SDS-PAGE and Western blotting analysis of whole-cell lysates of equal total protein prepared from S3I-201.1066-treated or untreated NIH3T3/v-Src and Panc-1 cells probing for pY705Stat3, Stat3, pY416Src, Src, pJak1, Jak1, pShc, Shc, pErk1/2 and Erk1/2. Positions of STATs:DNA complexes or proteins in gel are labeled; control lanes (0) represent nuclear extracts treated with 0.05% DMSO, or nuclear extracts or whole-cell lysates prepared from 0.05% DMSO-treated cells. Data are representative of 3-4 independent determinations. **—<0.01.

S3I201 analogs derived per in silico structural optimization and molecular modeling of the binding to the Stat3 SH2 domain were synthesized and evaluated in Stat3 DNA-binding assay in vitro, as previously done (18). Nuclear extracts containing activated Stat3 prepared from v-Src transformed mouse fibroblasts (NIH3T3/v-Src) that harbor aberrant Stat3 were incubated for 30 min at room temperature with or without increasing concentrations of the analogs, S3I201.1066 and S3I-201.2096, prior to incubation with the radiolabeled hSIE probe that binds to Stat3 and Stat1 and subjecting to electrophoretic mobility shift assay (EMSA) analysis (18). Stat3 DNA-binding activity was inhibited in a dose-dependent manner by both S3I-201.1066 and S3I201.2096 (FIG. 2A(i) and (ii)), with average $IC_{50}$ values of 35±09 µM and 45±12 µM, respectively. These values represent 2-3 fold improvement over the activity of the lead agent, S3I-201 ($IC_{50}$ of 86 µM) (18), from which the present compounds were derived. For selectivity, nuclear extracts containing activated Stat1, Stat3 and Stat5 prepared from EGF-stimulated NIH3T3/hEGFR (mouse fibroblasts over-expressing the human epidermal growth factor receptor, EGFR) were pre-incubated at room temperature with or without increasing concentrations of S3I-201.1066 for 30 min, prior to incubation with the radiolabeled oligonucleotide probes and subjecting to EMSA analyses, as previously done (18). EMSA results of the binding studies using the hSIE probe shows the strongest complex of Stat3:Stat3 with the probe (upper band, lanes 1 and 2), which is significantly disrupted at 50 µM S3I-201.1066 and completely disrupted at 100 µM S3I-201.1066 (FIG. 2A(iii), upper band, lanes 2 and 3). EMSA analysis further shows a less intense Stat1:Stat3 complex (intermediate band), which is similarly repressed at 50 µM and completely disrupted at 100 µM S3I-201.1066 (FIG. 2A(iii), lanes 2 and 3). By contrast, we observe no significant inhibition of the Stat1:Stat1 complex that is of the lowest intensity (lower band) at 50 µM S3I-201.1066, a moderate inhibition at 100 µM S3I-201.1066, while a complete inhibition occurred at 200 µM S3I-201.1066 (FIG. 2A(iii), lower band). Of importance, at the 100 µM S3I-201.1066 concentration at which only a moderate inhibition of Stat1:Stat1 complex occurred, the larger Stat3:Stat3 complex is completely dissociated (FIG. 2A, lane 3). Moreover, EMSA analysis showed no effect on Stat5:Stat5 complex with the MGFe probe, up to 300 µM S3I-201.1066 (FIG. 2A(iv)). Thus. S3I-201.1066 preferentially inhibits DNA-binding activity of Stat3 over that of Stat1 and Stat5.

Inhibition of Intracellular Stat3 Activation.

Stat3 is constitutively activated in a variety of malignant cells, including human breast and pancreatic cancer cells (9, 10, 20). Given the effect against Stat3 DNA-binding activity in vitro, we evaluated S3I-201.1066 in v-Src transformed mouse fibroblasts (NIH3T3/v-Src), human breast cancer (MDA-MB-231) and human pancreatic cancer (Panc-1) lines that harbor aberrant Stat3 activity.

Twenty-four hours after treatment, nuclear extracts were prepared from cells and subjected to Stat3 DNA-binding assay in vitro using the radiolabeled hSIE probe and analyzed by EMSA. Compared to the control (0.05% DMSO-treated cells, lane 1), nuclear extracts from S3I-201.1066-treated NIH3T3/v-Src, Panc-1 and MDA-MB-231 cells showed dose-dependent decreases of constitutive Stat3 activation, with significant inhibition at 50 µM S3I-201.1066 (FIG. 2B, compare lanes 2-5, 810, and 13-15 to their respective controls (0)). Luciferase reporter studies were performed to further determine the effect of S3I-201.1066 on Stat3 transcriptional activity.

Results show that treatment with S3I-201.1066 of the v-Src transformed mouse fibroblasts (NIH3T3/v-Src) that stably express the Stat3-dependent luciferase reporter (pLucTKS3) (33) significantly ($p<0.01$) repressed the induction of the Stat3-dependent reporter (FIG. 2C). SDS-PAGE and Western blot analysis further showed that treatment with S3I201.1066 for 24 h induced a concentration-dependent reduction of pTyr705Stat3 levels in NIH3T3/v-Src (FIG. 2C(i), top panel) and Panc-1 cells (FIG. 2C(ii), top panel), presumably through the blockade of Stat3 binding to pTyr motifs of receptors and the prevention of de novo phosphorylation by tyrosine kinases.

By contrast, immunoblotting analysis of whole-cell lysates from the two cell line models showed no significant effects of S3I-201.10866 on the phosphorylation of Src (pY416Src), Jak1 (pJak), Shc (pShc), and Erk1/2 (pErk1/2) under the same treatment conditions, (FIG. 2C (i) and (ii), panels 2-5 from the top), except the disappearance of pJak1 level in Panc-1 cells at 100 µM S3I201.1066. Total Stat3, Src, Jak1, Shc and Erk1/2 protein levels remained unchanged. We infer that at the concentrations that inhibit Stat3 activity. S3I-201.1066 has minimal effect on Src, Jak1, Shc and Erk1/2 activation.

In Vitro Evidence that S3I-201.1066 Interacts with Stat3 (or SH2 Domain) and Selectively Disrupts Stat3 Binding to Cognate pTyr Peptide Motif of Receptor.

Figure 3:
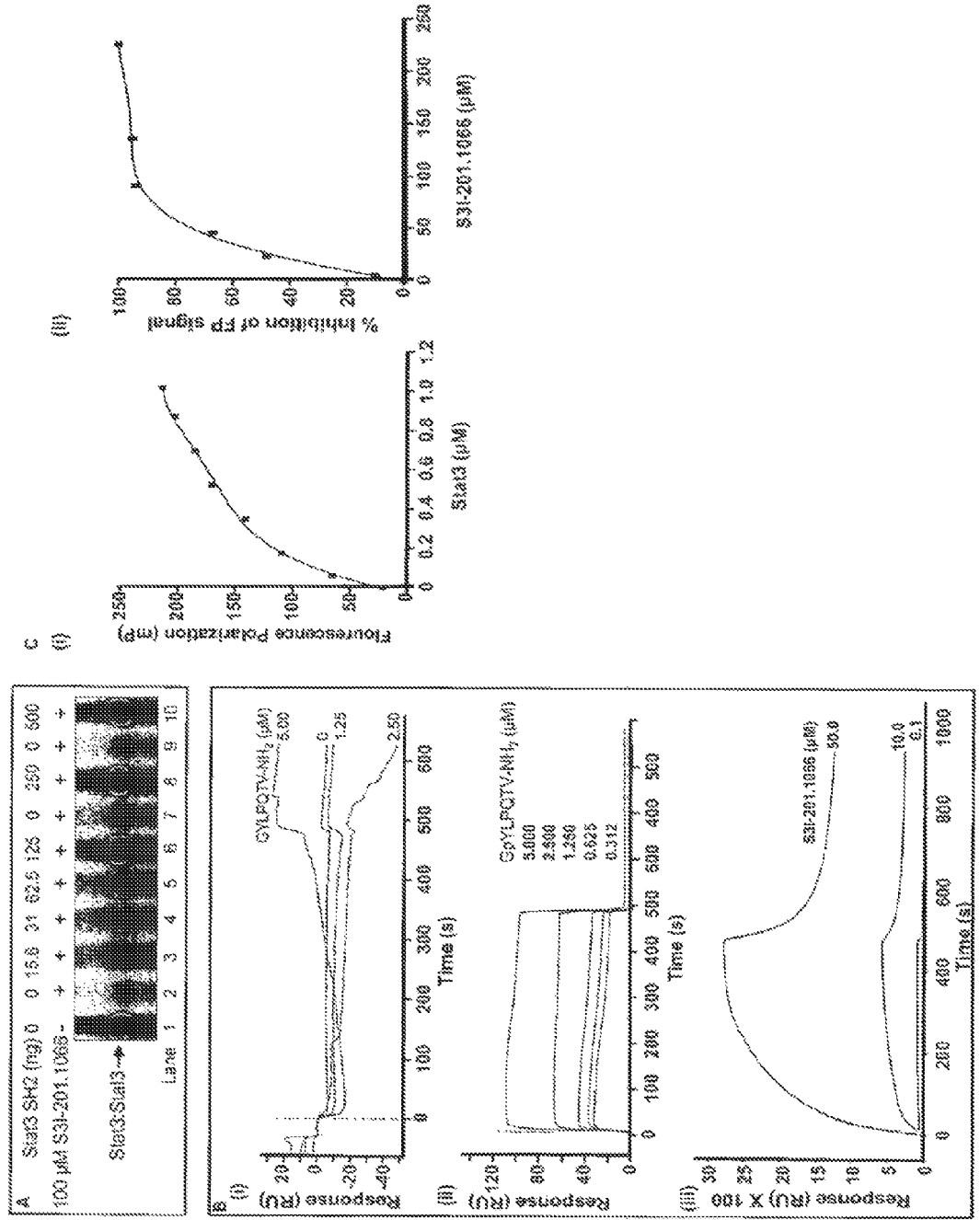
FIG. 3 depicts studies of the interaction of S31-201.1066 with Stat3 or the Stat3 SH2 domain. (A) EMSA analysis of in vitro binding of Stat3 to the radiolabeled hSIE probe using nuclear extracts containing activated Stat3 preincubated with 0-100 (μM S31-201.1066 in the presence or absence of increasing concentrations of purified His-tagged Stat3 SH2 domain; (B) Surface Plasmon Resonance analysis of the binding of (i) GYLPQTV-NH2 (SEQ ID NO:7) (unphosphorylated, high affinity gp-130 peptide), (ii) GpYLPQTV-NH2 (phosphorylated SEQ ID NO:7), or (iii) small-molecule 531-201.1066 as analyte to the purified His-tagged Stat3 immobilized on HisCap Sensor Chip; and (C) Fluorescence Polarization assay of the binding to the 5carboxyfluorescein GpYLPQTV-NH2 (phosphorylated SEQ ID NO:7) probe of (i) increasing concentration of purified His-Stat3 or (ii) a fixed amount of purified His-Stat3 (150 nM) in the presence of increasing concentrations of 531201.1066. Stat3:DNA complexes in gel are shown, control (−) lane or zero (0) represent 0.05% DMSO. Data are representative of 2-4 independent determinations.

Given the computational modeling prediction that S3I-201.1066 interacts with the Stat3 SH2 domain, we deduce that S3I201.1066 blocks Stat3 DNA-binding activity by binding to the Stat3 SH2 domain, thereby disrupting Stat3:Stat3 dimerization. To determine therefore if the Stat3 SH2 domain could interact with S3I-201.1066, we tested whether the addition of the recombinant Stat3 SH2 domain into the DNA-binding assay mixture could intercept the inhibitory effect of the agent on Stat3 activity that is observed in FIG. 2A(i). Purified histidine-tagged Stat3 SH2 domain (His-SH2) was added at increasing concentrations (1-500 ng) to nuclear extracts containing activated Stat3 and the mixed extracts were subjected to DNA-binding assay in vitro for the study of the effect of S3I-201.1066, as was done in FIG. 2A(i). EMSA analysis shows a strong inhibition by S3I-201.1066 of Stat3 DNA-binding activity, as shown in FIG. 2A(i), when no His-SH2 domain was added to the nuclear extracts (FIG. 3A, lanes 2, 7, and 9 compared to lane 1). By contrast, the observed S3I-201.0166-mediated inhibition of Stat3 DNA-binding activity was progressively eliminated by the presence of an increasing concentration of purified His-SH2 domain (Stat3 SH2), leading to the full recovery of Stat3 activity when recombinant SH2 domain protein was present at 125-500 ng (FIG. 3A, lanes 3-6, 8 and 10).

The preceding studies suggest that S3I-201.1066 interacts with the Stat3 SH2 domain. However, the studies do not demonstrate a direct binding to the Stat3 SH2 domain. To provide definitive evidence of direct binding to Stat3, biophysical studies were performed. H1s-tagged Stat3 protein (or SH2 domain; 50 ng) was immobilized on a Ni-NTA sensor chip surface for Surface Plasmon Resonance analysis of the binding of 531201.1066 as the analyte. Association and dissociation measurements were taken and the binding affinity of S31-201.1066 for Stat3 was determined using Qdat software. Results showed a gradual increase and decrease with time in the signals (response unit (RU)) for the association and dissociation, respectively, of the agent upon its addition to the immobilized His-Stat3 (FIG. 3B(iii)), indicative of the binding of S31-201.1066 to and dissociation from the Stat3 protein. The curves depicted interactions between Stat3 and S31-201.1066, with a binding affinity, $K_o$ of 2.74 nM/providing the first definitive evidence of direct Stat3 binding for S31-201 or its derivatives. The interactions also showed a dependency on the concentration of the S31-201.1066 (FIG. 3B(iii)). This SPR analysis of the conformational changes in His-Stat3 was validated by using the high affinity Stat3-binding phosphoTyr (pY) peptide, GpYLPQTV-NH2 (phosphorylated SEQ ID NO:7) derived from the interleukin-6 receptor (IL-6R) subunit, gp-130 (22,23) (with a $K_o$ of 24 nM) (FIG. 3B(ii)), and its non-phosphorylated counterpart, GYLPQTV-NH2 (SEQ ID NO:7), which showed little evidence of significant binding to Stat3 (FIG. 3B(i)). Interestingly, the dissociation curve for S31-201.1066 showed a large residual binding to Stat3 between 500-1000 s (FIG. 3B(iii), 10-50 µM, 500-1000 s), compared to the rapid association and dissociation of the high affinity peptide to and from Stat3 with no residual binding of the phosphopeptide (FIG. 3B(ii)). The implication of this finding is presently unknown, but may suggest a slower "off" rate for the dissociation of S31-201.1066 from Stat3. Differences in the chemical compositions and physicochemical properties would account for these different behaviors of interactions with the Stat3 protein.

The studies so far demonstrate that S31201.1066 interacts with Stat3 or the Stat3 SH2 domain (data not shown). The interaction with the Stat3 SH2 domain could block the binding of Stat3 to its cognate pTyr peptide motifs of receptors. To verify that the agent disrupts pTyr-Stat3 SH2 domain interactions, hence Stat3:Stat3 dimerization, we set up a fluorescence polarization (FP) study based on the binding of Stat3 to the high affinity 5 peptide, GpYLPQTV-NH2 (phosphorylated SEQ ID NO:7) (22,23). It has previously been reported that Stat3 binds to GpYLPQTV-NH2 (phosphorylated SEQ ID NO:7) with a higher affinity than to the Stat3-derived pTyr peptide, PpYLKTK (SEQ ID NO:8). This high affinity peptide disrupted Stat3 DNA-binding activity in vitro with an $IC_{50}$ value of 0.15 µM (22). The FP assay utilizing the 5carboxyfluorescein-GpYLPQTV-NH2 (phosphorylated SEQ ID NO:7) as a probe showed a saturation curve in the fluorescence polarization signal (mP) with increasing concentration (in µM) of purified His-Stat3 for a robust Z' value of 0.84 (FIG. 3C(i)), which closely matches the previously reported value of 0.87 (23).

Test of the non-phosphorylated, non-labeled GYLPQTV-NH2 (SEQ ID NO:7) in the FP assay showed no evidence of effect on the fluorescent polarization signal (data not shown), while as expected, the phosphorylated, unlabeled counterpart, GpYLPQTV-NH2 (phosphorylated SEQ ID NO:7) induced a complete inhibition with an $IC_{50}$ value of 0.3 µM (data not shown), consistent with the previously reported value of 0.25±0.03 µM (23). The FP assay was used to further test the computational modeling prediction of the ability of S31-201.1066 to disrupt Stat3 interaction with its cognate pTyr peptide. Results show that S31-201.1066, in a concentration-dependent manner, abrogated the fluorescent polarization signal for the interaction between the fluorescently-labeled phosphopeptide and Stat3 (FIG. 3C(ii)). The inhibitory constant ($IC_{50}$ value) was derived to be 20±7.3 µM, which is within the range for the $IC_{50}$ value (35±9 µM) determined for the inhibition of Stat3 DNA-binding activity (FIG. 2A(i)). These findings together indicate that S31-201.1066 binds to Stat3 or its SH2 domain and disrupts the interaction of Stat3 with its pTyr peptide, thereby blocking Stat3 DNA-binding activity.

Figure 4:
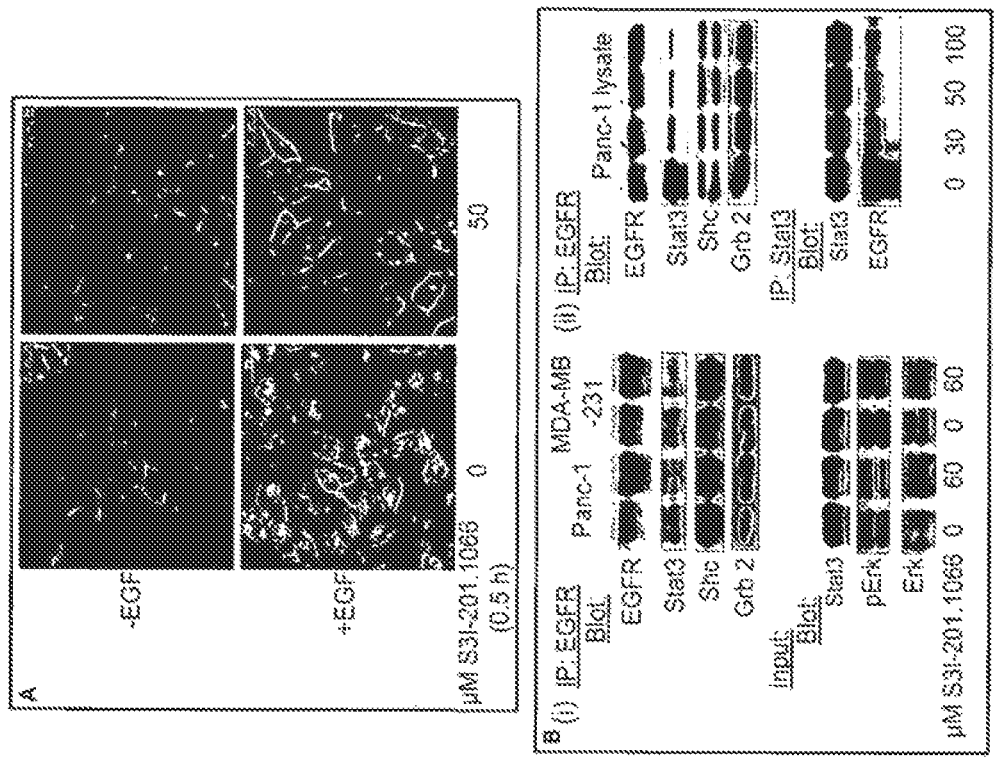
FIG. 4 shows the effect of S3I-201.1066 on the colocalization or association of Stat3 with EGF receptor and on Stat3 nuclear translocation. (A) Immunofluorescence imaging/confocal microscopy of Stat3 colocalization with EGFR and Stat3 nuclear localization in EGF-stimulated (1 g/ml; 10 min) NIH3T3/hEGFR pre-treated with or without 50 μM S3I-201.1066 for 30 min; or (B) Immunoblotting analysis of (i) EGFR immunecomplex (upper panel) or whole-cell lysates (lower panel) from S3I201.1066-treated Panc-1 and MDA-MB-231 cells, or (ii) immunecomplexes of EGFR (upper panel) or Stat3 (lower panel) treated with the indicated concentrations of S3I-201.1066 and probing for EGFR, Stat3, Shc, Grb 2, or Erk1/2MAPK. Data are representative of three independent studies.

To further verify that S3I-201.1066 disrupts the binding of Stat3 to receptors, mouse fibroblasts over-expressing the EGF receptor (NIH3T3/hEGFR) were treated with or without the compound prior to stimulation with EGF for 10 min. Cells were then subjected to immunostaining for EGFR (red) and Stat3 (green) and analyzed by confocal microscopy for EGF-induced colocalization of Stat3 and EGFR and for Stat3 nuclear translocation, as previously performed (17). In the resting NIH3T3/hEGFR fibroblasts, EGFR (red) is widely localized at the plasma membrane, while Stat3 (green) is localized at both the plasma membrane and in the cytoplasm, with a minimal colocalization with EGFR at the plasma membrane and no visible presence in the nucleus (stained blue for DAPI) (FIG. 4A upper panel). Stimulation by EGF of cells untreated with S3I-201.1066 induced a strong nuclear presence of Stat3 (cyan for merged Stat3 (green) and DAPI (blue)), as well as colocalizations of EGFR and Stat3 (yellow for merged EGFR (red) and Stat3 (green)) at the plasma membrane, cytoplasm, and peri-nuclear space (FIG. 4A, bottom left). This EGF-stimulated colocalization between EGFR and Stat3 and the Stat3 nuclear localization were both strongly blocked when cells were pre-treated with S3I-201.1066 before stimulating with EGF (FIG. 4A, bottom right compared to non-treated, bottom left), indicating that the compound disrupts Stat3 binding to EGFR. We infer that by blocking Stat3 binding to EGFR, S3I-201.1066 attenuates Stat3 phosphorylation/activation and thereby prevents Stat3 nuclear translocation. To investigate further the Stat3 interaction with the EGFR receptor and the effect of S3I-201.1066, coimmunoprecipitation with immunoblotting studies were performed in which EGFR immunecomplex was immunoprecipitated from whole-cell lysates prepared from treated and untreated cancer cells and blotted for Stat3, and for Shc and Grb 2 as negative control. Results showed that EGFR immunecomplex precipitated from untreated Panel and MDA-MB-231 cells contained Stat3, Shc and Grb 2 (FIG. 4B(i), lanes 1 and 3, i.p. EGFR, blot Stat3. Shc, and Grb 2). By contrast, treatment of both cell lines with S3I-201.1066 significantly diminished the level of Stat3 that associated with EGFR in the immunecomplex of equal total protein without affecting the Shc or Grb 2 levels that are associated with EGFR in the complex. See FIG. 4B(i), lanes 2 and 4, i.p. EGFR, blot Stat3, Shc and Grb 2. Western blotting of whole-cell lysates of equal total protein shows the levels of activated and total Erk1/2 are unaffected by the treatment of cells with S3I-201.1066 (FIG. 4B(i), input, blot pErk and Erk) and the Stat3 protein levels remain the same (FIG. 4B(i), input, blot Stat3).

In other studies, EGFR and Stat3 immunecomplexes were independently precipitated from whole-cell lysates of untreated Panc-1 cells and complexes of equal total protein were directly treated with 0-100 M S3I-201.1066 for 3 h and then subjected to Western blotting analysis. Compared to untreated samples (FIG. 4B(ii), lane 1), results show that the direct treatment with S3I-201.1066 of the EGFR immunecomplex dramatically diminished the level of Stat3 present in the complex (FIG. 4B(ii), i.p. EGFR, blot Stat3, lanes 2-4), with no visible changes in the levels of Shc or Grb 2 present in the complex (FIG. 4B(ii), i.p., EGFR, blot Shc or Grb 2). The EGFR levels in the immunecomplexes remained unchanged (FIG. 4B(ii), upper band). Similarly, the Stat3 immunecomplex that is directly treated with S3I-201.1066 and blotted for EGFR showed strongly reduced EGFR levels, compared to the untreated Stat3 immunecomplex of equal total protein (FIG. 4B(ii), i.p. Stat3, blot EGFR, compare lane 1 to lanes 2-4). The Stat3 levels in the immunecomplexes remained unchanged (FIG. 4B(ii), i.p. Stat3, blot Stat3). Altogether, these findings strongly indicate that S3I-201.1066 disrupts the binding of Stat3 to cognate receptor motifs, thereby blocking Stat3 phosphorylation and nuclear translocation.

S3I-201.1066 Blocks Growth, Viability, Malignant Transformation, and the Migration of Cells Harboring Constitutively-Active Stat3.

Aberrant Stat3 promotes malignant cell proliferation, survival and malignant transformation (10, 20, 42). Given that S3I201.1066 disrupts Stat3 activation, we asked the question whether this agent is able to selectively decrease the viability and growth of malignant cells that harbor aberrant Stat3 activity. The human breast (MDA-MB-231) and pancreatic cancer (Panc-1) lines and the v-Src-transformed mouse fibroblasts (NIH3T3/v-Src) that harbor constitutively-active Stat3, as well as cells that do not harbor aberrant Stat3 (normal mouse fibroblasts (NIH3T3), v-Ras-transformed counterpart fibroblasts (NIH3T3v-Ras), Stat3 knockout mouse embryonic fibroblasts (MEFs) (Stat3−/−) (31), normal human pancreatic duct epithelial cells (HPDEC) (30), and mouse thymic epithelial stromal cells (TE-71) cells (32)) in culture were treated with or without an increasing concentration of S3I-201.1066 for up to 6 days and analyzed for viable cell numbers by CyQuant cell proliferation/viability kit (FIG. 5A) and by trypan blue exclusion with phase-contrast microscopy (FIG. 5B), as described in the "Materials and Methods".

Figure 5:
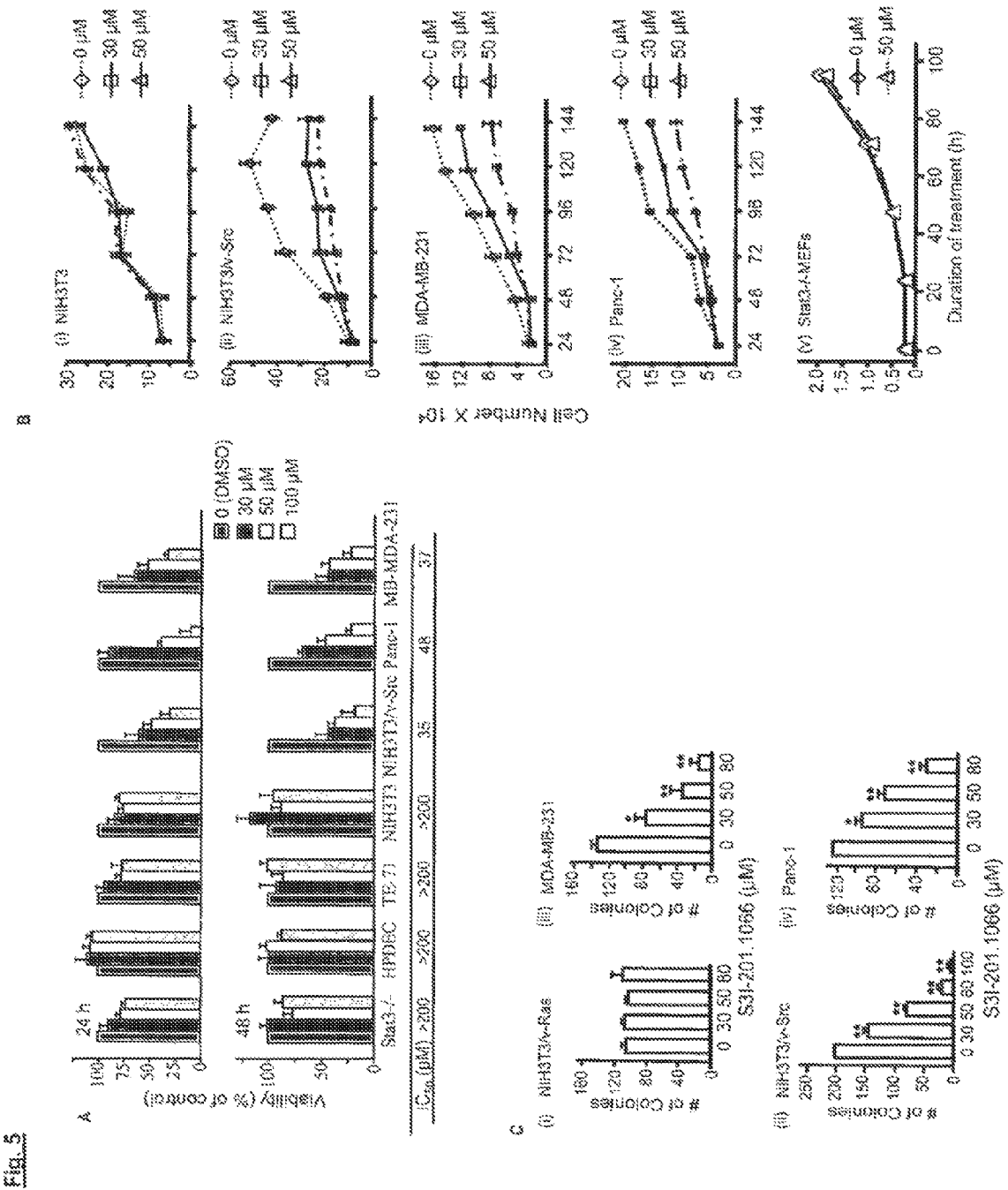
FIG. 5 indicates that S3I-201.1066 suppresses viability, growth and survival of malignant cells that harbor persistently-active Stat3 Human breast (MDA-MB-231) and pancreatic (Panc-1) cancer cells, the normal mouse fibroblasts (NIH3T3) and their v-Src transformed (NIH3T3/v-Src) or v-Ras transformed (NIH3T3/v-Ras) counterparts, mouse thymic epithelial stromal cells (TE-71), Stat3 null mouse embryonic fibroblasts (Stat3−/−), and the normal human pancreatic duct epithelial cells (HPDEC) were treated once or untreated with 30-100 M S3I-201.1066 for 24-144 h. Cells were (A) assayed for viability using CyQuant cell proliferation kit; $IC_{50}$ values were derived from graphical representation; (B) harvested at each 24-h period following treatment and viable cells counted by trypan blue exclusion with phase-contrast microscopy; or (C) allowed to culture until large colonies were visible, which were stained with crystal violet and enumerated. Values are the mean and S.D. of 3-4 independent determinations, p values, *—<0.05, and **—<0.01.

Compared to the control (DMSO-treated) cells, the mouse fibroblasts transformed by v-Src (NIH3T3/v-Src), and the MDA-MB-231 and Panc-1 cells showed significantly reduced viable cell numbers (FIG. 5A) and were growth inhibited (FIG. 5B(ii)-(iv)) following treatment with increasing concentrations of S3I-201.1066 for 24-144 h. By contrast, the viability (FIG. 5A) and growth (FIG. 5B(i) and (v)) of NIH3T3, Stat3-null MEFs (Stat3−/−), normal human pancreatic duct epithelial cells (HPDEC), and the mouse thymus epithelial stromal cells (TE71) that do harbor aberrant Stat3 activity were not significantly altered by up to 200 μM S3I201.1066 treatment (FIGS. 5A and B, and data not shown), with derived $IC_{60}$ values that are >200 μMm compared to 35, 48, and 37 μM for NIH3T3/v-Src, Panc-1, and MDA-MB-231, respectively (FIG. 5A, lower panel). These findings suggest that S3I-201.1066 exerts preferential biological effects against malignant cells that harbor constitutively-active Stat3, and at concentrations that inhibit Stat3 activity, the agent does not affect other cells.

We extended these studies to examine the effect of S3I-201.1066 in colony survival assay performed as previously reported (39). Cultured single-cells were untreated or treated once with S3I-201.1066 and allowed to grow until large colonies were visible, which were stained and enumerated.

Results showed a dose-dependent suppression of the number of colonies for the v-Src transformed mouse fibroblasts (NIH3T3/v-Src), the human pancreatic cancer, Panc-1 and the human breast cancer, MDA-MB-231 cells (FIG. 5C(ii)-(iv)). By contrast, minimal effect was observed on the colony numbers for mouse fibroblasts transformed by v-Ras (NIH3T3/v-Ras) that do not harbor constitutively-active Stat3 (FIG. 5C(i)). Furthermore, growth in soft-agar suspension of NIH3T3/v-Src, MDA-MB-231 and Panc-1 cells treated with S3I-201.1066 was significantly inhibited (FIG. 6A(ii)-(iv)). By comparison, at concentrations that inhibit Stat3, 53I-201.1066 showed minimal effect on the soft-agar growth of v-Ras transformed mouse fibroblasts (NIH3T3/v-Ras) (FIG. 6A(i)). These findings indicate that S3I-201.1066 selectively suppresses viability, growth, and survival of malignant cells harboring aberrant Stat3, and blocks Stat3-mediated malignant transformation. Thus, these studies demonstrate that Stat3 is important not only for tumor growth, but also tumor progression (43,44).

Figure 6:
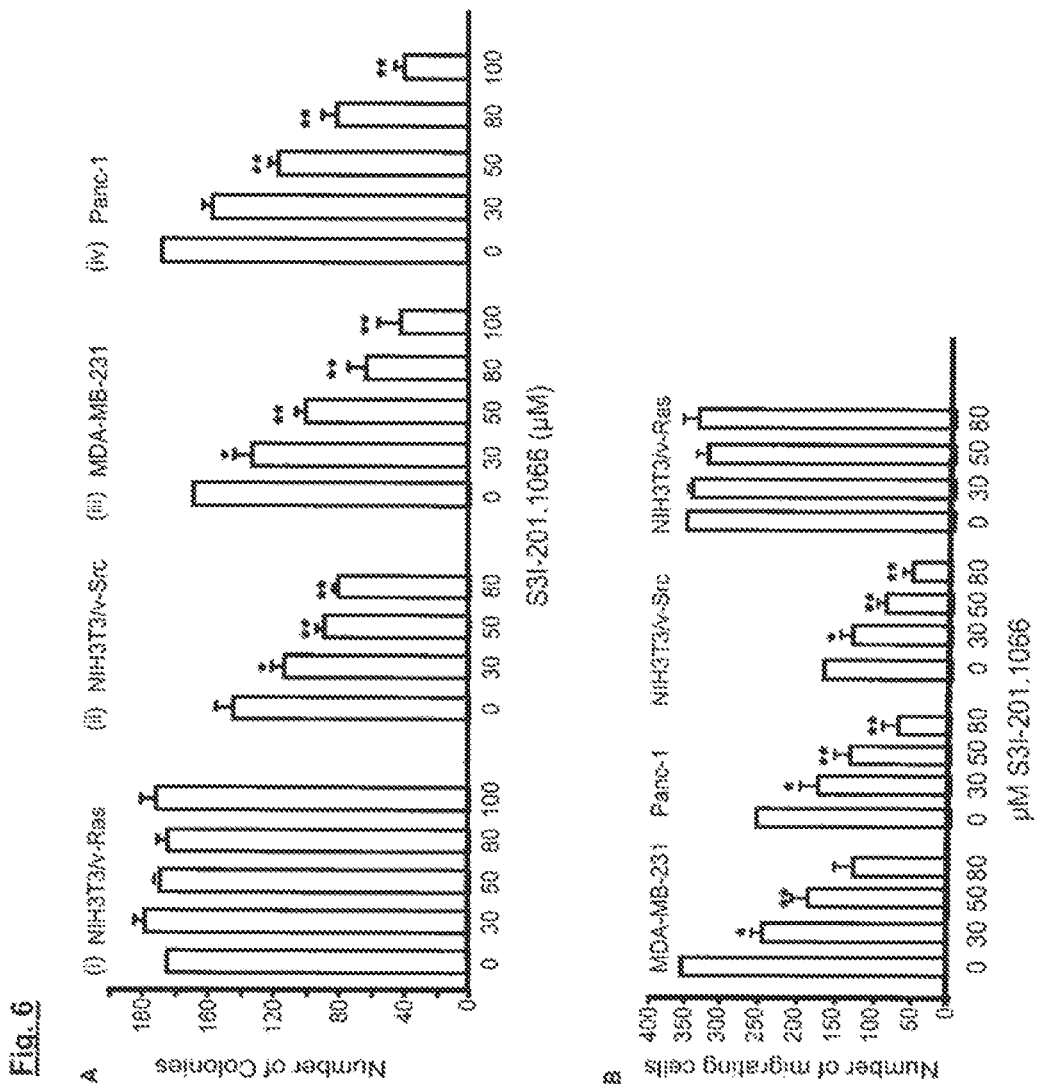
FIG. 6 demonstrates that S3I-201.1066 blocks Stat3-dependent malignant transformation and inhibits the migration of malignant cells harboring aberrant Stat3. (A) Viral Src-transformed mouse fibroblasts (NIH3T3/v-Src) and counterpart transformed by v-Ras (NIH3T3/v-Ras) growing in soft-agar suspension were treated with or without 30-100 μM S3I-201.1066 every 2-3 days until large colonies were visible, which were stained with crystal violet and enumerated; (B) Wound healing assay for effect on cell migration in which human breast (MDA-MB-231) and pancreatic (Panc-1) cancer cells, and the v-Src transformed mouse fibroblasts (NIH3T3/v-Src) and counterparts transformed by v-Ras (NIH3T3/v-Ras) were treated with or without 30-80 μM S3I-201.1066 for 12-24 h and allowed to migrate into the denuded area. Cell migration was visualized at 10× magnification by light microscopy and cells that migrated into the denuded area counted and plotted against the concentration of S3I-201.1066. Values are the mean and S.D. of 3 independent determinations. p values, *—<0.05, and **—<0.01.

To further investigate the biological effects of S3I-201.1066 and to assess the ability to block Stat3-dependent tumor progression processes, a wound healing study was performed, as described in "Materials and Methods" section for monitoring the migration of malignant cells and the effect of treatment with S3I-201.1066. Significantly reduced numbers of MDA-MB-231, Panc-1 and NIH3T3/v-Src cells migrating into the denuded area were observed following 12-24 h treatment with S3I-201.1066 (FIG. 6B and data not shown), with strongly reduced numbers occurring at 50 or 100 μM S3I201.1066 treatment, and statistically lower numbers at 30 M S3I-201.1066 (FIG. 6B). By contrast, the migration of NIH3T3/v-Ras fibroblasts was minimally affected by the same treatment conditions (FIG. 6B). In the 12-24 h treatment duration, there was no evidence of apoptosis of the treated cells (data not shown). These findings demonstrate that S3I-201.1066 selectively suppresses the migration of malignant cells that harbor aberrant Stat3.

S3I-201.1066 Represses the Expression of c-Myc, Bcl-xL, VEGF, and MMP-9.

Figure 7:
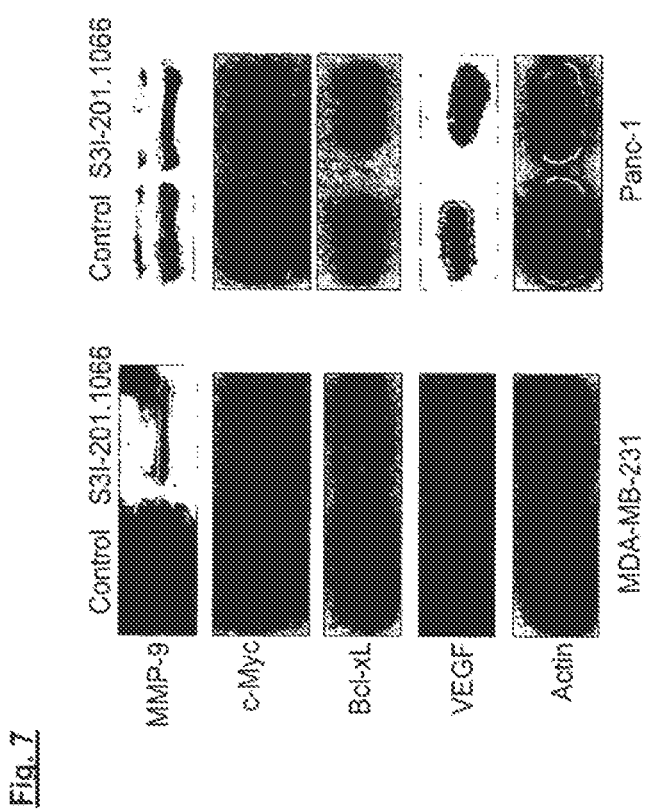
FIG. 7 shows that S3I-201.1066 suppresses c-Myc, Bcl-xL, MMP-9 and VEGF expression. SDS-PAGE and Western blotting analysis of whole-cell lysates prepared from the human breast cancer MDA-MB-231 and pancreatic cancer Panc-1 cells untreated (DMSO, control) or treated with 80-100 μM S3I-201.1066 for 48 h and probing with anti-Myc, Bcl-xL, MMP-9, VEGF or R-actin antibodies. Positions of proteins in gel are shown. Data are representative of 3 independent determinations.

Known Stat3 downstream target genes are key in the dysregulated biological processes promoted by aberrant Stat3 (9, 20, 42). We sought to validate the inhibitory effect of S3I-201.1066 on aberrant Stat3 signaling and to define the underlying molecular mechanisms for the antitumor cell effects of the agent by investigating changes in the induction of known Stat3-regulated genes. In the human breast carcinoma, MDA-MB-231 and pancreatic cancer, Panc-1 cell lines that harbor constitutively-active Stat3, immunoblotting analysis of whole-cell lysates shows the constitutive induction of known Stat3-regulated genes, including c-Myc, Bcl-xL, VEGF, and MMP-9 proteins, which were significantly suppressed in response to 48 h-treatment with S3I-201.1066 (FIG. 7 and data not shown). These data indicate that S3I-201.1066 sufficiently represses the constitutive induction of Stat3-regulated genes, thereby thwarting the effect of aberrant Stat3 in terms of eliminating the dysregulation of growth and survival that supports the malignant phenotype. The ability of S3I-201.1066 to block Stat3 transcriptional activity is also supported by the data in FIG. 2C.

S3I-201.1066 Inhibits Growth of Human Breast Tumor Xenografts.

Figure 8:
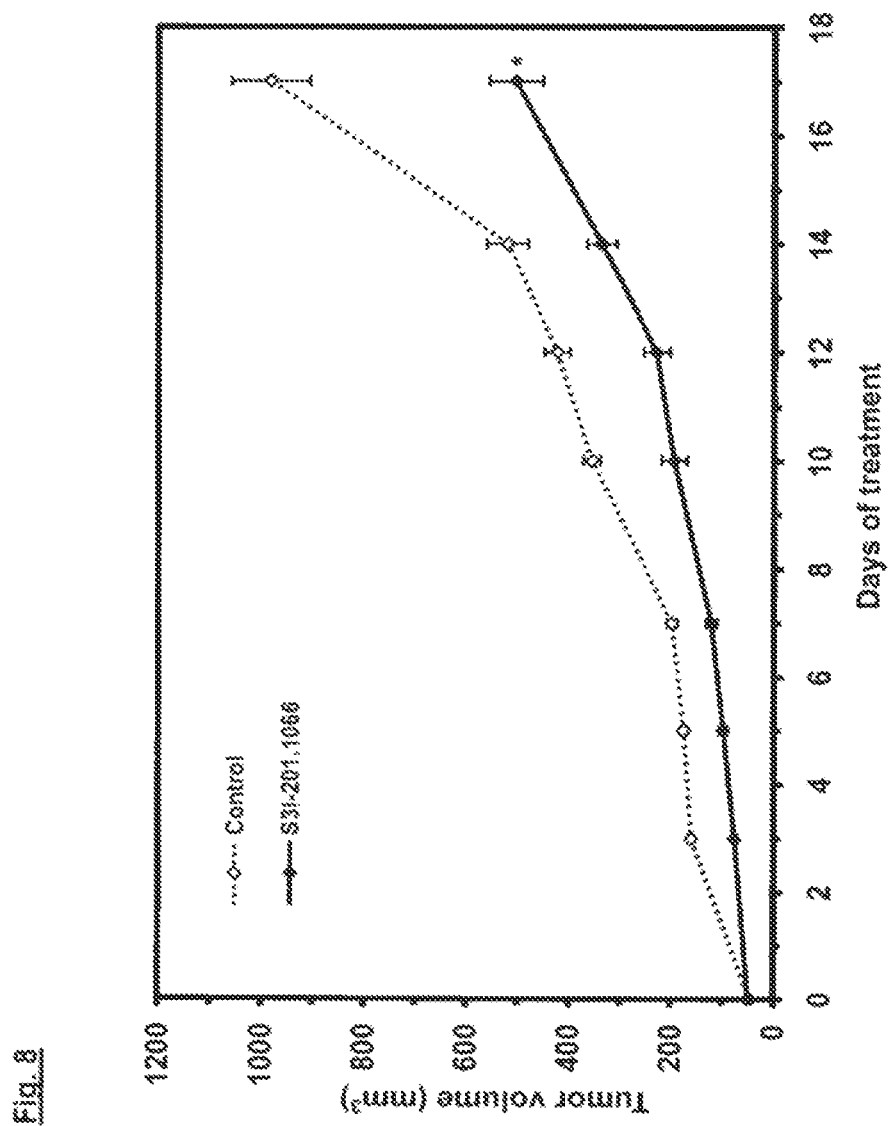
FIG. 8 shows that S3I-M2001 inhibits growth of human breast tumor xenografts. Human breast (MDA-MB231) tumor-bearing mice were given S3I-201.1066 (3 mg kg-1) or vehicle (0.1% DMSO in PBS) i.v. every 2 or 3 days. Tumor sizes, measured every 2 or 3 days, were converted to tumor volumes and plotted against treatment days; Values are the mean and S.D. from replicates of 12 tumor-bearing mice in each group. *<0.05.

Given Stat3's importance in tumor growth and tumor progression, we evaluated S3I-201.1066 in xenograft models of the human breast cancer (MDA-MB-231) cells that harbor aberrant Stat3. Compared to control (vehicle-treated), tumor-bearing mice, treated (i.v. injection) with S3I-201.1066 at 3 mg/kg every 2 or 3 days for 17 days had greatly reduced tumor sizes (FIG. 8). Animals remained viable at this dose and showed no obvious sign of toxicity. These findings together demonstrate that S3I-201.1066 induces antitumor cell effects and tumor regression by targeting the Stat3 SH2 domain and thereby inhibiting Stat3-mediated tumor processes.

DISCUSSION

Computational modeling of the interactions of the Stat3 SH2 domain with the previously reported Stat3 inhibitor lead, S3I-201 (18) derived key structural information for optimization and a rational synthetic program that furnished exciting new analogs. The compounds disclosed herein. S3I-201.1066 (Formula 1) and S3I-201.2096 (Formula 2) show improved Stat3-inhibitory potency and selectivity in vitro, with intracellular Stat3-inhibitory activity that is enhanced 2-3-fold. Analog S3I-201.1066 exhibited an improved target selectivity and showed a minimum inhibitory effect on the phosphorylation of Src, Jak1, Erk1/2MAPK and Shc proteins at concentrations (30-50 µM) that inhibit intracellular Stat3 activation, despite there being SH2 domains involved in the mechanisms leading to the activation of these other proteins. Per molecular modeling, the improved activity could in part be due to the enhanced interactions with the Stat3 protein, possibly by the (para cyclohexyl)benzyl moiety that extends from the scaffold amide nitrogen and makes important contacts with the hydrophobic residues Trp623, Ile659, Val637 and Phe716 within the unexplored pocket.

The native Stat3 peptide inhibitor, PpYLKTK (SEQ ID NO:8) (where pY represents pTyr) and its peptidomimetic analogs (15,16) and several other Stat3 SH2 domain-binding and dimerization disrupting peptides and their derivatives have been reported (21,22,25). Previous studies have utilized the fluorescence polarization analysis to characterize the binding of the native, high affinity phosphopeptide, GpYLPQTV-NH2 (phosphorylated SEQ ID NO:7) (as 5carboxyfluorescein-GpYLPQ TV-NH2 (phosphorylated SEQ ID NO:7)) to the Stat3 protein (22,23). Using this assay platform and surface plasmon resonance analysis, we provide definitive evidence for the physical interaction of S3I-201.1066 with Stat3 or its SH2 domain, with an affinity (KD) of 2.3 µM.

The analysis of the interaction reveals a slower kinetics of the association and dissociation, which contrasts the more rapid binding and dissociation of the native, high affinity peptide, GpYLPQTV-NH2 (phosphorylated SEQ ID NO:7) to and from Stat3, with a corresponding affinity (KD) of 24 nM. The implication of these differences in the binding kinetics in relation to the modulation of Stat3 function is presently unclear.

The second supporting evidence for the interaction of S3I201.1066 with Stat3 comes by way of the disruption by S3I-201.1066 of the Stat3 binding to the pTyr peptide in a fluorescent polarization assay based on the high affinity peptide, 5carboxyfluorescein-GpYLPQTV-NH2 (phosphorylated SEQ ID NO:7) probe and Stat3, with a derived $IC_{50}$ of 45 µM.

By comparison, the unlabeled, native phosphopeptide disrupts this interaction between the probe and Stat3, with an $IC_{50}$ value of 0.3 µM, which is in line with similar reported studies of the high affinity peptide (22,23) that derived an affinity of 0.15±0.01 µM (23) and an IC50 value of 0.290±0.063 µM (21). The higher affinity of the native peptide for the protein should be expected, given the more favorable physicochemical properties that will facilitate a stronger binding to the Stat3 protein.

Overall, our study provides support for the binding of S3I-201.1066 to Stat3, and for its ability to disrupt the interaction between Stat3 and its cognate pTyr peptide, an event that is indicative of Stat3: Stat3 dimerization. Although other Stat3 dimerization disruptors have been previously identified through molecular modeling (19,45), the present study is the first to provide biophysical evidence for a direct interaction of a small-molecule, dimerization disruptor with the Stat3 protein. Given the disruption of the Stat3 binding to the cognate peptide, GpYLPQTV-NH2 (phosphorylated SEQ ID NO:7), we infer that inside cells, S3I-201.1066 may interfere with the ability of Stat3 (via SH2 domain) to bind to cognate pTyr motifs on receptors and thereby block de novo phosphorylation by tyrosine kinases, as well as disrupt pre-existing Stat3: Stat3 dimers, particularly in malignant cells that harbor aberrant Stat3. Indeed, our study shows a strong association of Stat3 with EGFR in ligand-stimulated mouse fibroblasts or in cancer cells, and a strong presence in the nucleus of stimulated cells. Both the Stat3:EGFR association and the Stat3 nuclear presence are blocked by S31201.1066, indicating that by disrupting Stat3 binding to receptors, S31-201.1066 prevents Stat3 phosphorylation, activation, and nuclear translocation, thereby attenuating Stat3 function.

Substantive evidence demonstrates that aberrant Stat3 activity promotes cancer cell growth and survival (15, 16, 29, 46, 47), and induces tumor angiogenesis (48,49) and metastasis (43,49). Accordingly, inhibitors of Stat3 activation and signaling have been shown to induce antitumor cell effects consistent with the abrogation of Stat3 function (15-19, 37, 50-52).

The present disclosure parallels these published reports in showing that S3I-201.1066 induces growth inhibition and loss of viability and survival of the human pancreatic cancer Panc-1 and breast cancer MDA-MB-231 cells, and of the v-Src transformed mouse fibroblasts (NIH3T3/v-Src), which are restricted to malignant cells that harbor aberrant Stat3, while the effects on normal human pancreatic duct epithelial cells, normal mouse fibroblasts, mouse thymic epithelial stromal cells, the viral Ras-transformed mouse fibroblasts that do not harbor aberrant Stat3, and the Stat3 knockout mouse embryonic fibroblasts (Stat3−/−) (31) are minimal.

Moreover, S3I-201.1066-induced antitumor cell effects occurred at significantly lower concentrations, 30-50 µM, than the 100 µM activity previously reported for the lead agent (18). Mechanistic insight into the is biological effects of S3I-201.1066 as a Stat3 inhibitor is provided by the evidence of a suppression of the constitutive expression of known Stat3-regulated genes, including c-Myc, Bcl-xL, VEGF and MMP-9, and the disruption of the Stat3 binding to receptor, which control cell growth and apoptosis, promote tumor angiogenesis, or modulate invasion (19, 43, 46, 49, 53, 54). The exclusion of Stat3 from the nucleus further contributes to the inhibition of Stat3 transcriptional function. We further note the significant antitumor effect of S3I-201.1066 in human breast tumor xenografts. Altogether the present disclosure provides evidence for the binding of S3I-201.1066 to Stat3, disruption of Stat3:pTyr interactions and hence Stat3: Stat3 dimerization, and the disruption of the Stat3 binding to receptor, phosphorylation and nuclear translocation.

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

REFERENCES CITED

1. Bromberg, J. (2000) Breast Cancer Res. 2, 86-90.
2. Darnell, J. E., Jr. (2002) Nat. Rev. Cancer 2, 740-749.
3. Schroder, M., Kroeger, K., Volk, H. D., Eidne, K. A., and Grütz, G. (2004) J. Leukoc Biol. 75, 792-797.
4. Sehgal, P. B. (2008) Dev Biol 19, 329-340.

5. Bromberg, J., and Darnell. J. E., Jr. (2000) Oncogene 19, 2468-2473.
6. Bowman, T., Garcia, R., Turkson, J., and Jove, R. (2000) Oncogene 19, 2474-2488.
7. Turkson, J., and Jove, R. (2000) Oncogene 19, 6613-6626.
8. Buettner, R., Mora, L. B., and Jove. R. (2002) Clin. Cancer Res. 8, 945-954.
9. Yu, H., and Jove, R. (2004) Nat. Rev. Cancer 4, 97-105.
10. Turkson, J. (2004) Expert Opin Ther Targets 8, 409-422.
11. Darnell, J. E. (2005) Nat Med. 11, 595-596.
12. Kortylewski, M., and Yu, H. (2007) J Immunother. 30, 131-139.
13. Kortylewski, M., and Yu, H. (2008) Curr Opin Immunol. 20, 228-233.
14. Shuai, K., Horvath, C. M., Huang, L. H., Qureshi, S. A., Cowburn, D., and Darnell, J E., Jr (1994) Cell 76, 821-828.
15. Turkson. J., Ryan, D., Kim, J. S., Zhang, Y., Chen, Z., Haura, E., Laudano, A., Sebti, S., Hamilton, A. D., and Jove. R. (2001) J. Biol. Chem. 276, 45443-45455.
16. Turkson. J., Kim, J. S., Zhang, S., Yuan, J., Huang, M., Glenn, M., Haura, E., Sebti, S., Hamilton, A. D., and Jove, R. (2004) Mol Cancer Ther 3, 261-269.
17. Siddiquee, K., Glenn, M., Gunning, P., Katt, W. P., Zhang, S., Schroeck, C., Jove, R., Sebti, S., Hamilton, A. D., and Turkson, J. (2007) ACS Chem Biol. 2 787-798.
18. Siddiquee, K., Zhang, S., Guida, W. C., Blaskovich. M. A., Greedy, B., Lawrence, H., Yip, M. L. R., Jove, R., McLaughlin, M., Lawrence, N., Sebti, S., and Turkson, J. (2007) 1: Proc Natl Acad Sci USA. 104 7391-7396.
19. Song, H., Wang, R., Wang, S., and Lin, J. (2005) Proc Natl Acad Sci USA. 102, 47004705.
20. Yue, P., and Turkson, J. (2009) Expert Opin Investig Drugs. 18 45-56.
21. Coleman, D. R. I., Ren, Z., Mandal, P. K., Cameron, A. G., Dyer, G. A., Muranjan, S., Campbell, M., Chen, X., and McMurray, J. S. (2005) J. Med. Chem. 48, 6661-6670.
22. Ren. Z., Cabell, L. A., Schaefer, T. S., and McMurray, J. S. (2003) Bioorg Med Chem Lett 13, 633-636.
23. Schust, J., and Berg, T. (2004) Anal. Biochem. 330 114-118.
24. Gunning, P. T., Glenn, M. P., Siddiquee, K. A., Katt. W. P., Masson, E., Sebti, S. M., Turkson, J., and Hamilton, A. D. (2008) Chembiochem. 9, 2800-2803.
25. Fletcher, S., Turkson, J., and Gunning. P. T. (2008) Chem Med Chem 3, 1159-1168.
26. Becker, S., Groner, B., and Muller, C. W. (1998) Nature 394, 145-151.
27. Johnson, P. J., Coussens, P. M., Danko, A. V., and Shalloway, D. (1985) Mol. Cell. Biol. 5, 1073-1083.
28. Yu, C. L., Meyer, D. J., Campbell, G. S., Lamer, A. C., Carter-Su, C., Schwartz, J., and Jove. R. (1995) Science 269, 81-83.
29. Garcia, R., Bowman, T. L., Niu, G., Yu, H., Minton, S., Muro-Cacho, C. A., Cox, C. E., Falcone, R., Fairclough, R., Parson, S., Laudano, A., Gazit, A., Levitzki, A., Kraker, A., and Jove, R. (2001) Oncogene 20, 2499-2513.
30. Ouyang, H., Mou, L. J., Luk, C., Liu, N., Karaskova, J., Squire, J., and Tsao, M. S. (2000) Am. J. Pathol. 157, 1623-1631.
31. Maritano, D., Sugrue, M. L., Tininini, S., Dewilde, S., Strobi, B., Fu, X., Murray-Tait, V., Chiarle, R., and Poll, V. (2004) Nat Immunol. 5, 401-409.
32. Farr, A. G., Hosier, S., Braddy. S. C., Anderson, S. K., Eisenhardt, D. J., Yan, Z. J., and Robles, C. P. (1989) Cell Immunol. 119, 427-444.
33. Turkson, J., Bowman, T., Garcia, R., Caldenhoven, E., De Groot, R. P., and Jove, R. (1998) Mol. Cell. Biol. 18, 2545-2552.
34. Wagner, M., Kleeff, J., Friess, H., Buchler, M. W., and Korc, M. (1999) Pancreas, 19, 370-376.
35. Gouilleux, F., Moritz. D., Humar, M., Moriggl, R., Berchtold, S., and Groner, B. (1995) Endocrinology 136, 5700-5708.
36. Seidel, H. M., Milocco, L. H., Lamb, P., Darnell. J. E., Jr., Stein, R. B., and Rosen, J. (1995) Proc. Natl. Acad. Sci. U.S.A. 92, 3041-3045.
37. Turkson, J., Zhang, S., Mora, L. B., Burns, A., Sebti. S., and Jove, R. (2005) J Biol Chem. 280, 32979-32988.
38. Zhang, Y., Turkson, J., Carter-Su, C., Smithgall, T., Levitzki, A., Kraker, A., Krolewski, J. J., Medveczky, P., and Jove, R. (2000) J. Biol. Chem. 275, 24935-24944.
39. Zhao, S., Venkatasubbarao, K., Lazor, J. W., Sperry, J., Jin, C., Cao. L., and Freeman, J. W. (2008) Cancer Res 68, 4221-4228.
40. Jones, G., Willett, P., Glen, R. C., Leach, A. R., and Taylor, R. (1997) J. Mol. Biol. 267, 727-748.
41. Fletcher, S., Jardeephi, S., Zhang, X., Yue. P., Page, B. D., Sharmeen, S., Shahani, V., Schimmer, A., Turkson, J., and Gunning, P. T. (2009) Chem Bio Chem 10, 1959-1964.
42. Siddiquee, K. A. Z. and Turkson, J. (2008) Cell Res. 18, 254-267.
43. Xie, T. X., Wei, D., Liu, M., Gao, A. C., Ali-Osman, F., Sawaya, R., and Huang, S. (2004) Oncogene 23, 3550-3560.
44. Huang, C., Cao, J., Huang, K. J., Zhang, F., Jiang, T., Zhu, L., and Qiu, Z. J. (2006) Cancer Sci 97, 1417-1423.
45. Bhasin, D., Cisek, K., Pandharkar, T., Regan, N., Li, C., Pandit, B., Lin, J., and Li, P. (2008) Bioorg. Med. Chem. Lett. 18, 391-395.
46. Catlett-Falcone, R., Landowski, T. H., Oshiro, M. M., Turkson, J., Levitzki, A., Savino, R., Ciliberto, G., Moscinski, L., Fernandez-Luna, J. L., Nuñez, G., Dalton, W. S., and Jove, R. (1999) Immunity 10, 105-115.
47. More, L. B., Buettner, R., Seigne, J., Diaz, J., Ahmad, N., Garcia, R., Bowman, T., Falcone, R., Fairclough, R., Cantor, A., Muro-Cacho, C., Livingston, S., Karras, J., Pow-Sang. J., and Jove, R. (2002) Cancer Res 62, 6659-6666.
48. Niu, G., Wright, K. L., Huang, M., Song, L., Haura, E., Turkson, J., Zhang, S., Wang, T., Sinibaldi, D., Coppola, D., Heller, R., Ellis, L. M., Karras, 10 J., Bromberg, J., Pardoll, D., Jove, R., and Yu, H. (2002) Oncogene 21, 2000-2008.
49. Wei, D., Le, X., Zheng, L., Wang, L., Frey, J. A., Gao, A. C., Peng, Z., Huang, S., Xiong, H. Q., Abbruzzese, J. L., and Xie, K. (2003) Oncogene 22, 319-329.
50. Fuh, B., Sobo, M., Con, L., Josiah, D., Hutzen, B., Cisek, K., Bhasin, D., Regan, N., Lin, L., Chan, C., Caldas, H., DeAngelis, S., Li, C., Li, P., and Lin, J. (2009) Br. J. Cancer 100, 106-112.
51. Blaskovich, M. A., Sun, J., Cantor, A., Turkson. J., Jove, R., and Sebti, S. M. (2003) Cancer Res 63, 1270-1279.
52. Sun, J., Blaskovich, M. A., Jove, R., Livingston, S. K., Coppola, D., and Sebti, S. M. (2005) Oncogene. 24, 3236-3245.
53. Real, P. J., Sierra, A., De Juan, A., Segovia. J. C., Lopez-Vega, J. M., and Fernandez-Luna, J. L. (2002) Oncogene 21, 7611-7618.
54. Gritsko T, Williams A, Turkson J, Kaneko S. Bowman T, Huang M, Nam S, Eweis I, Diaz N, Sullivan D, Yoder S, Enkemann S, Eschrich S, Lee J H, Beam C A, Cheng J, Minton S, Muro-Cacho C. A., and Jove, R. (2006) Clin Cancer Res. 12, 11-19.

That which is claimed is:

1. A method effective to inhibit a cancer cell, comprising the step of contacting the cell with a compound and salts thereof according to Formula 1 or Formula 2:

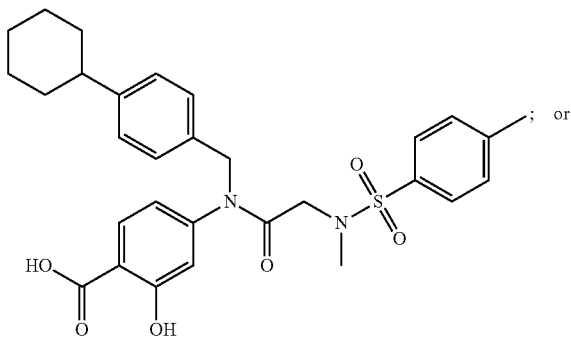

Formula 1

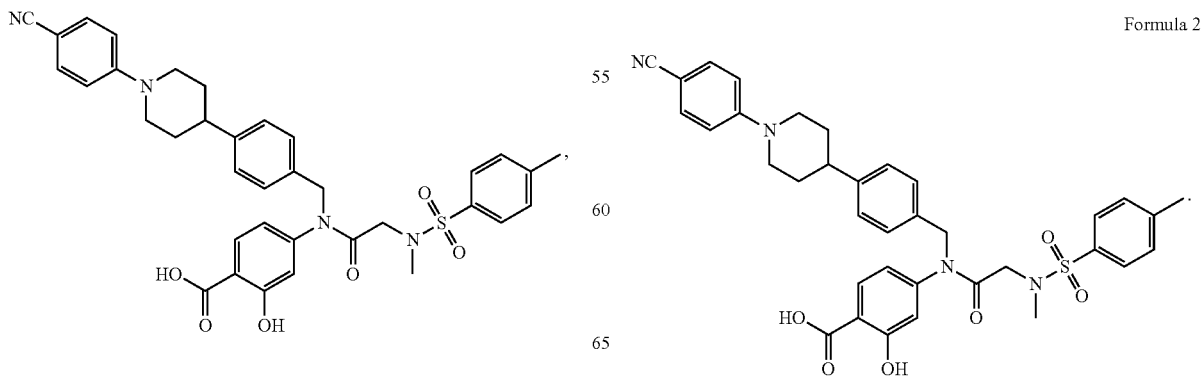

Formula 2 thereby inhibiting the cancer cell.

2. The method of claim 1, wherein the compound and salts thereof is according to Formula 1

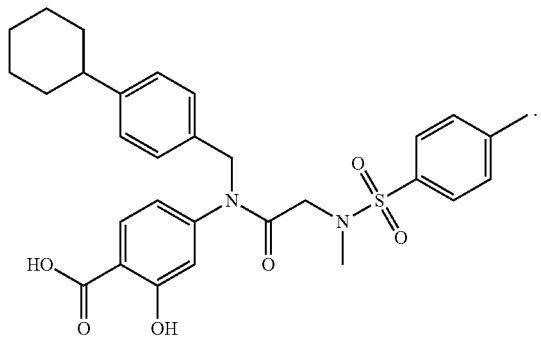

Formula 1

3. The method of claim 1, wherein the compound and salts thereof is according to Formula 2

Formula 2

4. The method of claim 1, wherein the cancer cell is a human pancreatic cancer cell.

5. The method of claim 1, wherein the cancer cell is a human breast cancer cell.

6. The method of claim 1, wherein the cancer cell is characterized by an aberrant level of Stat3.

7. A method effective to inhibit Stat3 activity in a cell, comprising the step of contacting the cell with a compound and salts thereof according to Formula 1 or Formula 2:

Formula 1

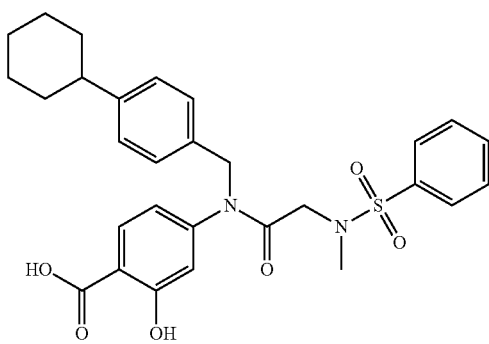

; or

Formula 2

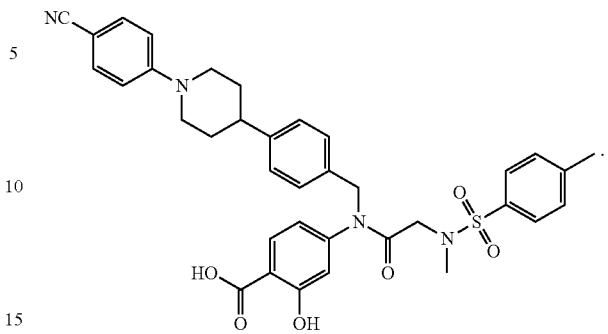

, thereby inhibiting Stat3 in the cell.

8. The method of claim 7, wherein the compound and salts thereof is according to Formula 1

Formula 1

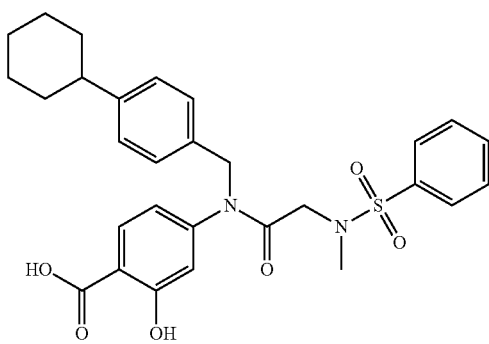

.

9. The method of claim 7, wherein the compound and salts thereof is according to Formula 2

Formula 2

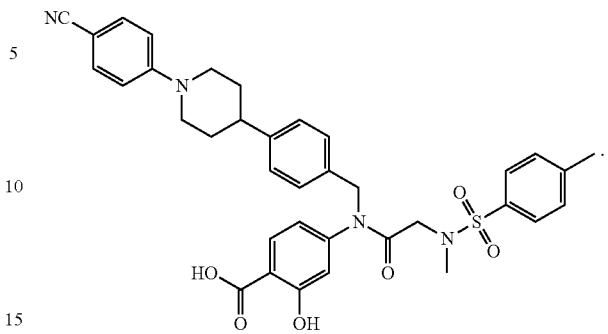

.

10. The method of claim 7, wherein the cell is a cancer cell.

11. The method of claim 10, wherein the cancer cell is a human pancreatic cancer cell.

12. The method of claim 10, wherein the cancer cell is a human breast cancer cell.

13. The method of claim 7, wherein the Stat3 is constitutively active.

14. A method effective to down-regulate the expression of Stat3-regulated genes in a cell, comprising the step of contacting the cell with a compound and salts thereof according to Formula 1 or Formula 2:

Formula 1

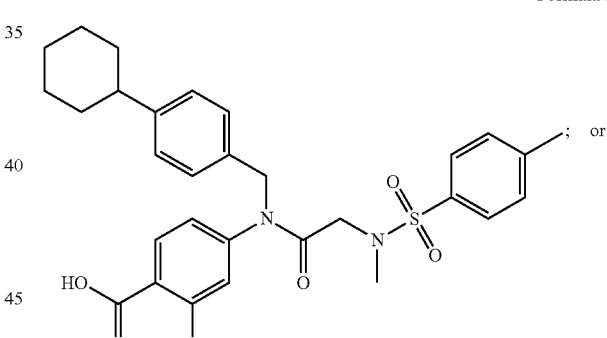

; or

Formula 2

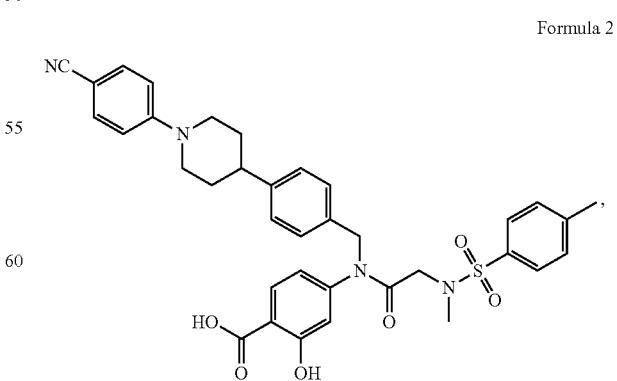

, thereby down-regulating Stat3 regulated genes in the cell.

15. The method of claim 14, wherein the compound and salts thereof is according to Formula 1

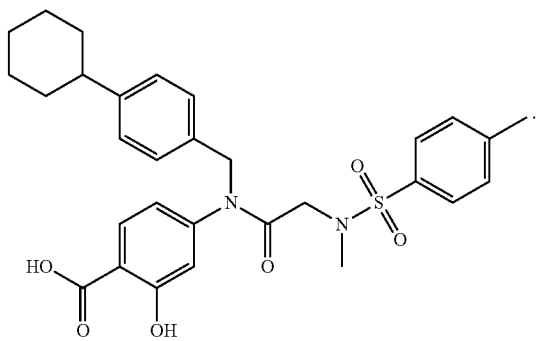

Formula 1

16. The method of claim 14, wherein the compound and salts thereof is according to Formula 2

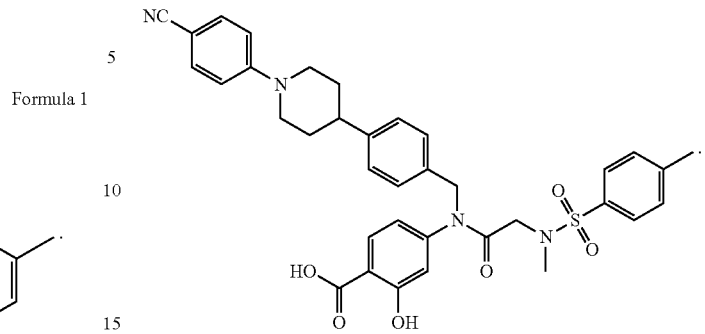

Formula 2

17. The method of claim 14, wherein the cell is a cancer cell.

18. The method of claim 17, wherein the cancer cell is a human pancreatic cancer cell.

19. The method of claim 17, wherein the cancer cell is a human breast cancer cell.

20. The method of claim 14, wherein the Stat3-regulated genes comprise c-Myc, Bcl.xL, matrix metalloproteinase 9, VEGF, or combinations thereof.

* * * * *

SEQUENCE LISTING

<160> NUMBER OF SEQ ID NOS: 8

<210> SEQ ID NO 1
<211> LENGTH: 34
<212> TYPE: DNA
<213> ORGANISM: Artificial Sequence
<220> FEATURE:
<223> OTHER INFORMATION: synthetic construct; Murine, PCR amplification
      primer, Stat3 Protein Forward

<400> SEQUENCE: 1
gacgacgaca agatggctca gtggaaccag ctgc                                   34

<210> SEQ ID NO 2
<211> LENGTH: 40
<212> TYPE: DNA
<213> ORGANISM: Artificial Sequence
<220> FEATURE:
<223> OTHER INFORMATION: synthetic construct; Murine, PCR amplification
      primer, Stat3 Protein Reverse

<400> SEQUENCE: 2
gaggagaagc ccggttatca catgggggag gtagcacact                             40

<210> SEQ ID NO 3
<211> LENGTH: 20
<212> TYPE: DNA
<213> ORGANISM: Artificial Sequence
<220> FEATURE:
<223> OTHER INFORMATION: synthetic construct; Murine, PCR Primer for
      Stat3-SH2 domain, Forward

<400> SEQUENCE: 3
atgggtttca tcagcaagga                                                   20

<210> SEQ ID NO 4
<211> LENGTH: 24
<212> TYPE: DNA
<213> ORGANISM: Artificial Sequence
<220> FEATURE:
<223> OTHER INFORMATION: synthetic construct; Murine, PCR Primer for
      Stat3-SH2 domain, Reverse

<400> SEQUENCE: 4
tcacctacag tactttccaa atgc                                              24

<210> SEQ ID NO 5
<211> LENGTH: 24
<212> TYPE: DNA
<213> ORGANISM: Artificial Sequence
<220> FEATURE:
<223> OTHER INFORMATION: synthetic construct; high affinity sis-
      inducible element from c-fos gene

<400> SEQUENCE: 5
agcttcattt cccgtaaatc ccta                                              24

<210> SEQ ID NO 6
<211> LENGTH: 18
<212> TYPE: DNA
<213> ORGANISM: Artificial Sequence
<220> FEATURE:
<223> OTHER INFORMATION: synthetic construct; Bovine beta-casein gene
      promoter for Stat1 and Stat5

<400> SEQUENCE: 6
agatttctag gaattcaa                                                     18

```
<210> SEQ ID NO 7
<211> LENGTH: 7
<212> TYPE: PRT
<213> ORGANISM: Artificial Sequence
<220> FEATURE:
<223> OTHER INFORMATION: synthetic construct; gp130 peptide
<220> FEATURE:
<221> NAME/KEY: MISC_FEATURE
<222> LOCATION: (2)..(2)
<223> OTHER INFORMATION: Y at position 2 can be phosphorylated

<400> SEQUENCE: 7

Gly Tyr Leu Pro Gln Thr Val
1               5

<210> SEQ ID NO 8
<211> LENGTH: 6
<212> TYPE: PRT
<213> ORGANISM: Artificial Sequence
<220> FEATURE:
<223> OTHER INFORMATION: synthetic construct; Stat3 derived pTyr peptide
<220> FEATURE:
<221> NAME/KEY: MISC_FEATURE
<222> LOCATION: (2)..(2)
<223> OTHER INFORMATION: Y at position 2 is phosphorylated

<400> SEQUENCE: 8

Pro Tyr Leu Lys Thr Lys
1               5
```